United States Patent
Shoshtaev et al.

(10) Patent No.: US 12,185,942 B2
(45) Date of Patent: Jan. 7, 2025

(54) KNOTLESS ORTHOPEDIC STABILIZATION SYSTEM

(71) Applicant: Dunamis Medical Technologies, LLC, Greenville, AL (US)

(72) Inventors: Eugene Shoshtaev, Del Mar, CA (US); Prithviraj Chavan, Greenville, AL (US); Forrest B. Samuel, Carlsbad, CA (US)

(73) Assignee: Dunamis Medical Technologies, LLC, Greenville, AL (US)

( * ) Notice: Subject to any disclaimer, the term of this patent is extended or adjusted under 35 U.S.C. 154(b) by 0 days.

(21) Appl. No.: 18/509,117

(22) Filed: Nov. 14, 2023

(65) Prior Publication Data
US 2024/0074747 A1     Mar. 7, 2024

Related U.S. Application Data

(63) Continuation of application No. 17/376,060, filed on Jul. 14, 2021, now Pat. No. 11,812,946, which is a continuation of application No. 15/909,773, filed on Mar. 1, 2018, now Pat. No. 11,109,855.

(60) Provisional application No. 62/465,337, filed on Mar. 1, 2017.

(51) Int. Cl.
*A61B 17/04* (2006.01)
*A61B 90/00* (2016.01)

(52) U.S. Cl.
CPC ...... *A61B 17/0487* (2013.01); *A61B 17/0401* (2013.01); *A61B 2017/0404* (2013.01); *A61B 2017/0409* (2013.01); *A61B 2017/0417* (2013.01); *A61B 2017/0451* (2013.01); *A61B 2017/0495* (2013.01); *A61B 2017/0496* (2013.01); *A61B 2090/061* (2016.02); *A61B 2090/062* (2016.02)

(58) Field of Classification Search
CPC ............ A61B 17/0401; A61B 17/0487; A61B 2017/0404; A61B 2017/0409; A61B 2017/0414; A61B 2017/0417; A61B 2017/0451; A61B 2017/0495; A61B 2017/0496; A61B 2090/061; A61B 2090/062
See application file for complete search history.

(56) References Cited

U.S. PATENT DOCUMENTS

2013/0035720 A1* 2/2013 Perriello ............... A61F 2/0811
606/232

\* cited by examiner

*Primary Examiner* — Mohamed G Gabr
(74) *Attorney, Agent, or Firm* — Jay B. Bell

(57) ABSTRACT

Button-suture assemblies which employ a knotted locking mechanism do not maintain tension when securing bone and tissue fragments. A knotless method and device for maintaining tension and providing precise placement of a button-suture assembly during stabilization procedures comprising a locking pin, which mates with a button creating pinch points with increased surface area through which suture can pass from a baseplate through two dedicated openings in the button, one for the first end of the suture and one for the second end of the suture while preventing tension loss during the locking step and therefore allowing for precise placement of the button-suture assembly.

12 Claims, 19 Drawing Sheets

KNOTLESS ORTHOPEDIC STABILIZATION SYSTEM

CROSS-REFERENCE TO RELATED APPLICATIONS

This application is a continuation of U.S. patent application Ser. No. 17/376,060, filed on Jul. 13, 2021 (now issued as U.S. Pat. No. 11,812,946), which is a continuation of U.S. patent application Ser. No. 15/909,773, filed on Mar. 1, 2018 (now issued as U.S. Pat. No. 11,109,855), which claims priority to U.S. Provisional Application No. 62/465,337 filed on Mar. 1, 2017, the contents of which are incorporated herein by reference in its entirety.

FIELD OF THE INVENTION

The present invention is generally directed toward a device and method for use in a surgical repair of bone or tissue. More particularly, the present invention relates to the stabilization of two or more bone or tissue fragments via an adjustable button-suture assembly.

BACKGROUND OF THE INVENTION

Bone suspension devices, such as button-suture assemblies, that stabilize bone and tissue are known in the art. The current devices secure the bone by locking the suture in place via a knot. In these procedures, after a hole is drilled through the bone, sutures are passed through it and fixated on the distal side of the hole. The bones are then pulled closer together and a knot is tied on the proximal side of the assembly to hold the tension. Tying a knot to hold the suture tight is relatively difficult and can result in some of the tension being lost as the knot is completed and the tying mechanisms (whether tool or fingers) release their grip on the suture. As a result, the loop of the knot springs back or relaxes one or more millimeters before the assembly is secured, and then resulting tension is significantly less than the tension initially intended.

Knotless systems also exist that employ various mechanisms for length adjustment and locking. In most of these, either the strength of the construct (measured by tension to failure) or its stability (by way of loss of tension) are sacrificed in favor of attaining better ease of use.

SUMMARY OF THE INVENTION

Assemblies that secure bone and tissue fragments lose tension before the assemblies can lock resulting in inefficient placement of the assembly during surgical procedures. The presently disclosed invention is a method and device comprising sutures manipulated through a baseplate on one end and locking pin mated with a button on the other to allow tensioning the construct and causing it to automatically lock when the applied tension is released and using a mechanism that utilizes the construct tension generated during the tensioning step to securely lock the construct by means of pinch points designed to maximize the tensile strength of the construct by increasing the surface area of contact between the suture and the locking elements and decreasing the stress that the suture is exposed to in the locked state.

BRIEF DESCRIPTION OF THE DRAWINGS

Further advantages of the invention will become apparent by reference to the detailed description of preferred embodiments when considered in conjunction with the drawings:

FIG. 7A depicts a cross sectional view of the button-suture assembly being tensioned. FIG. 7B depicts a cross-sectional view of the suspension device in locked position.

FIG. 8A depicts a cross sectional view of the locking pin being removed from the button. FIG. 8B depicts a cross-sectional view of the button-suture assembly in unlocked position.

FIG. 11A depicts a perspective view of an embodiment of the button-suture assembly and footprint extender. FIG. 11B depicts a perspective view of an embodiment of the button-suture assembly and footprint extender.

FIG. 12A depicts a perspective view of the button-suture with footprint extender. FIG. 12B depicts a perspective view of the button-suture with footprint extender. FIG. 12C depicts a perspective view of the button being pulled through the foot print extender. FIG. 12D depicts a cross-sectional view of the button inside the foot print extender.

FIG. 13A depicts a cross sectional view of the embodiment. FIG. 13B depicts a cross sectional view of the embodiment.

FIG. 18A depicts a perspective view of the expandable sounder instrument. FIG. 18B depicts a cross-sectional view of the expandable sounder instrument. FIG. 18C depicts a cross-sectional view of the tip of the expandable sounder instrument inserted into bone.

FIG. 19A depicts a perspective view of the button inserter/flipper. FIG. 19B depicts a cross-sectional view of the button inserter/flipper. FIG. 19C depicts a perspective view of the tip of the button inserter/flipper holding a button-suture assembly. FIG. 19D depicts a bottom perspective view of the tip of the button inserter/flipper holding a button-suture assembly. FIG. 19E depicts a cross-sectional view of the button-suture assembly being flipped outside a bone hole.

DETAILED DESCRIPTION

Figure 1:
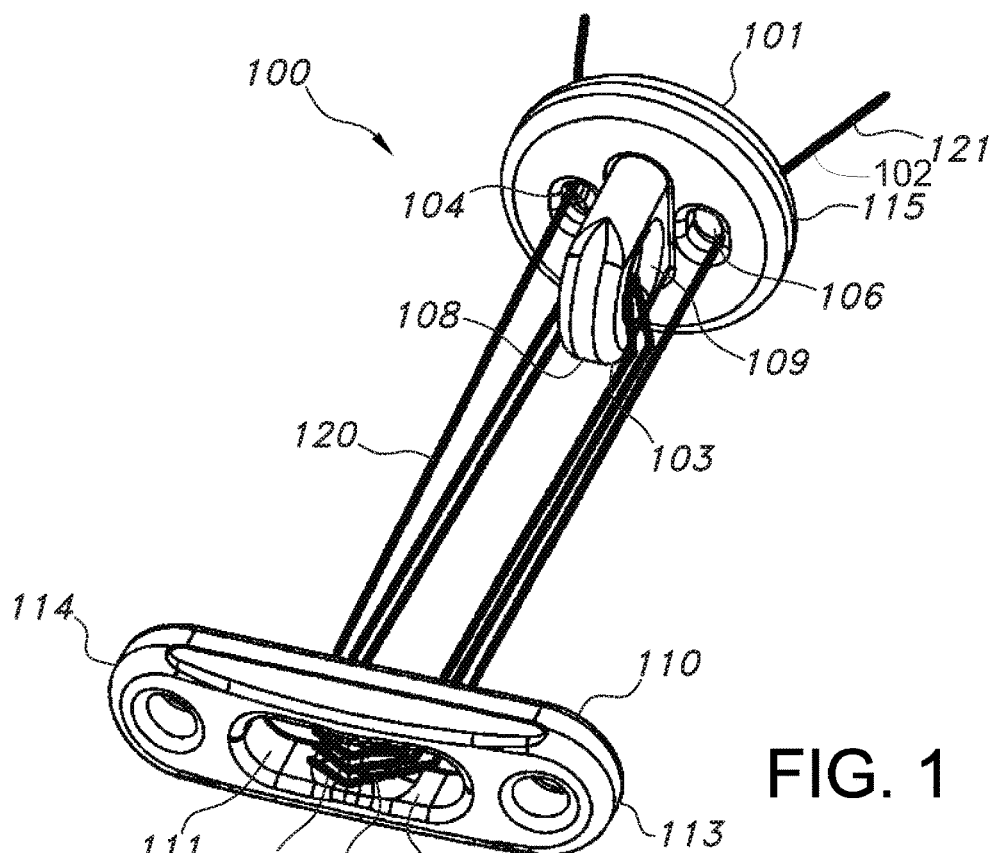
FIG. 1 depicts the preferred embodiment of the button-suture assembly.

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Knotted button-suture assemblies lose tension after the knot is tied on the proximal side of the assembly during surgical procedures. Tying a knot in the sutures during surgery can be substantially difficult and, as previously described, may result in loss of tension after the knot is tied as it is released by the tying implements. This loss in tension allows the loop to relax or spring back at least one or more millimeters making the placement of the assembly during the surgical procedure less precise. The button-suture assembly 100, described herein allows decreasing the length of suture loops 124, 125 and 126 between the baseplate 110 and the button 101 and locking pin 103 sub-assembly (henceforth referred to as suspension device 115) by means of pulling on loose suture ends 121, which results in suture loops 124 and 125 moving relative to the baseplate 110, but in the suture loops 124, 125 and 126 preferably not moving relative to the locking pin 103 through transverse aperture 109 of which it passes.

At a state when the proximal surface of the baseplate 110 and the distal surface of the button 101 make contact with bone surfaces, applying tension (pulling force) in the proximal direction to the loose suture ends 121, causes the locking pin 103 to translate proximally relative to the button 101 by a small amount that is preferably greater than zero but less than 1 mm and more preferably less than 0.50 mm and most preferably less than 0.25 mm. This proximal translation of the locking pin 103 is caused by the fact that the spacing between the loose suture ends 121 as they enter the button 101 (this spacing afforded them by openings 104 and 105 in the button 103 through which the loose suture ends 121 pass), is smaller than the spacing allowed by the proximal end of the locking pin 103 as the loose suture ends 121 exit the suspension device 115 (best seen in an embodiment in FIG. 7A). Since the loose suture ends 121 are pulled in generally proximal direction during the tensioning step, this difference in spacing causes the suture ends to exert a proximally-directed force on the locking pin 103.

Figure 4:
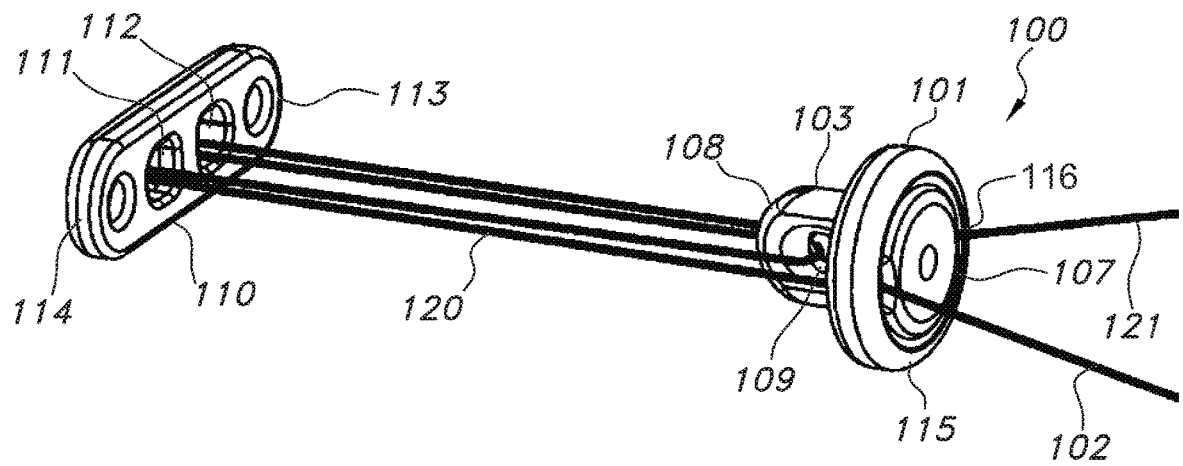
FIG. 4 depicts a perspective view of an embodiment of the button-suture assembly.
Figure 5:
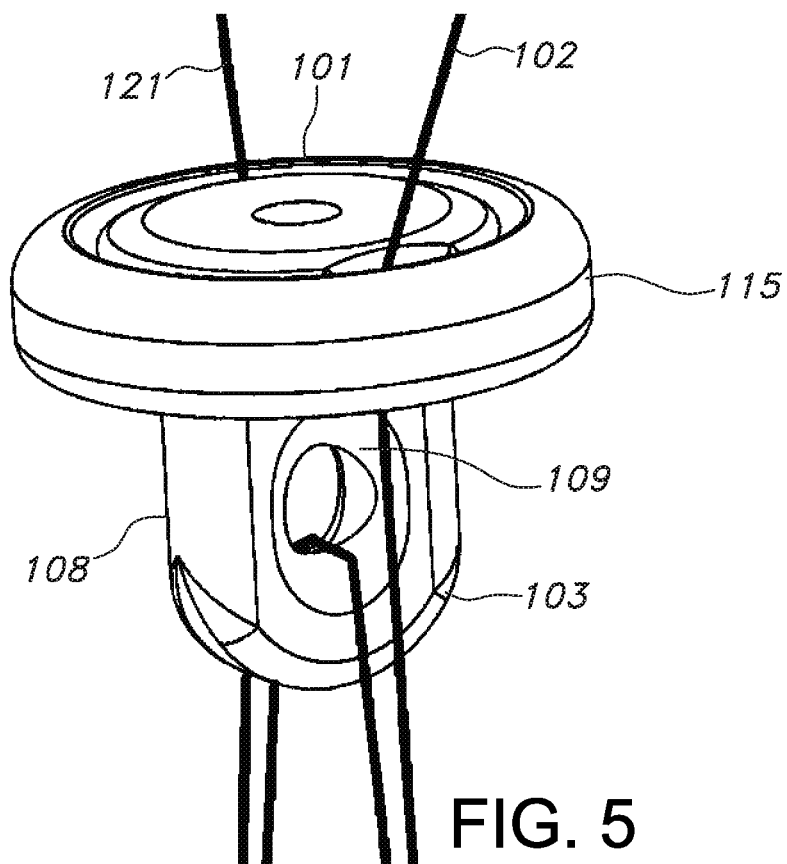
FIG. 5 depicts a perspective view of the locking pin of the button-suture assembly.
Figure 7A:
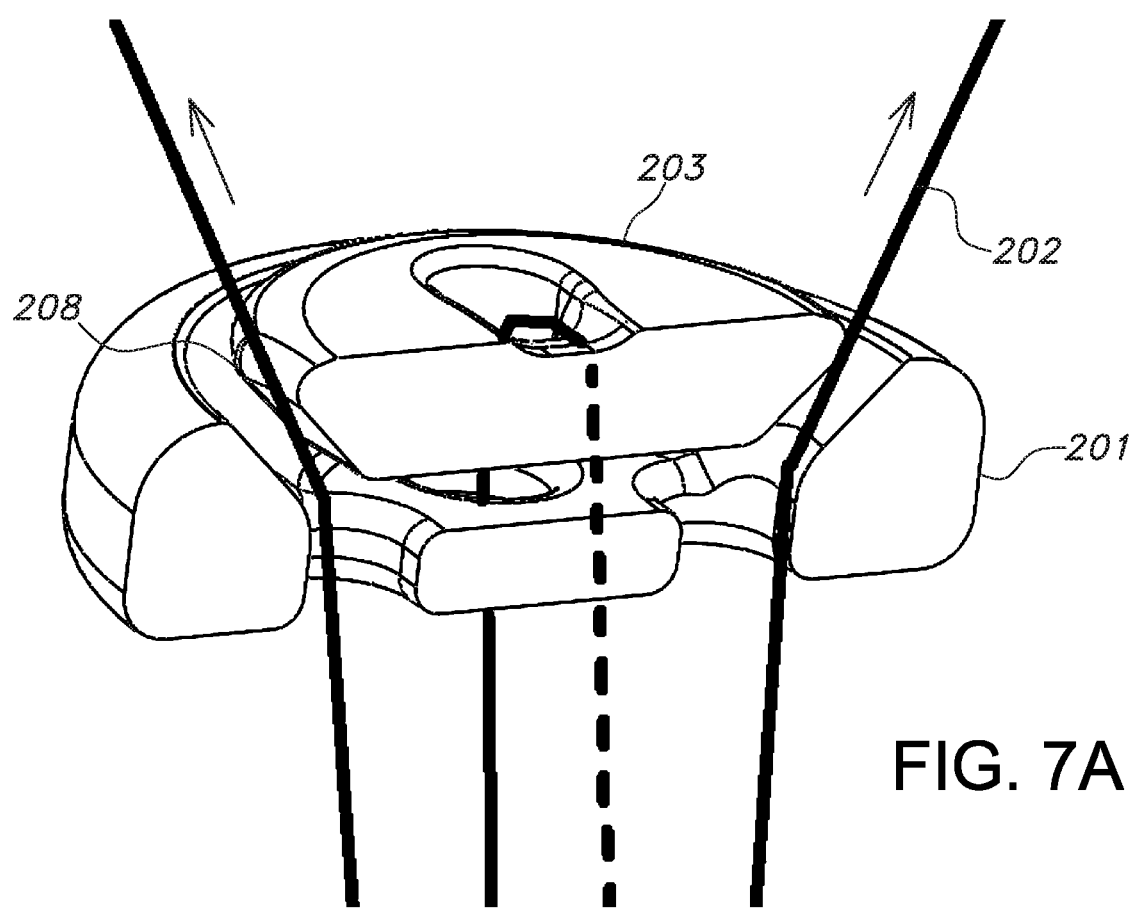
FIGS. 7A-7B depict the locking mechanism of the suspension device of the button-suture assembly. Individually.
Figure 7B:
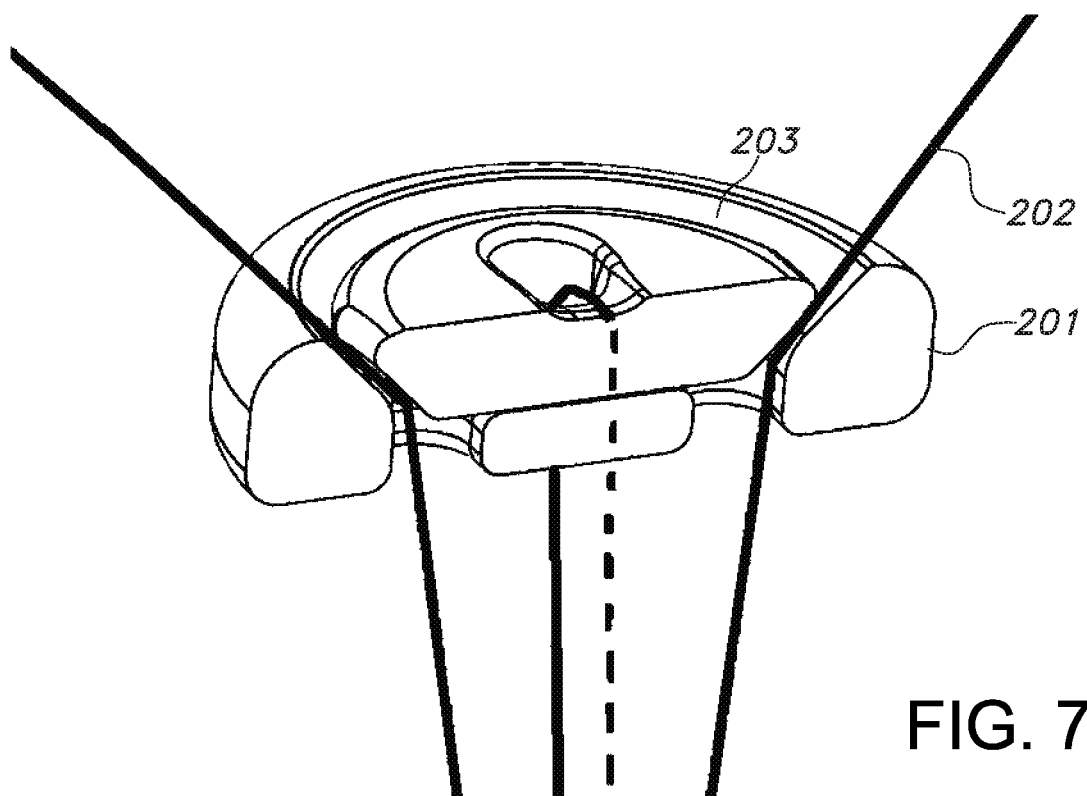

When the tension applied to the suture ends is released, the tension stored in the suture loops 124, 125 and 126 (which also results in compressive forces on the bony anatomy by the baseplate 110 and the button 103) causes the locking pin 103 to translate distally thereby bottoming out on and applying pressure to the suture 102 around pinch points 119 shown for example in FIG. 4 and causing the assembly to lock and to resist further lengthening of the suture loops 124, 125 and 126 (best seen in an embodiment in FIG. 7B). It should be understood that the amount by which the locking pin 103 moves proximally during the tensioning step and the amount by which the locking pin 103 moves distally when the tension on the loose suture ends 121 is released is contemplated to be the amount by which the assembly will "spring back" or relax as discussed above. Therefore, the lower the proximal displacement of the locking pin 103 required to pull the suture 102 through the suspension device 115—the lower the relaxation the full assembly will experience during the locking step.

Furthermore, it is contemplated that the size of elongate central opening 105 in the button 101 could prevent the suture loop 124, 125 and 126 from passing through it resulting in a stable assembly where the locking pin 103 cannot be completely withdrawn from the button 101 after assembly and while the suture loop 124, 125 and 126 passes through transverse opening 109 within it. Furthermore, due to each of the loose suture ends 121 passing through their own dedicated openings 104 and 106 in the button 101, the assembly functions in a predictable manner where the suture ends and the locking pin 103 translate through the button 101 in preferably one dimension (generally in proximal and distal directions).

The button-suture assembly 100 is used for knotless stabilization of two or more tissue, bone or other body members. While the preferred embodiment is contemplated for the stabilization of two bone or tissue fragments, the button-suture assembly is versatile and can be used for a variety of different applications. In the procedure utilizing the preferred embodiment of the button-suture assembly 100, a hole is drilled through bones, sutures are passed through the hole and fixated on the distal side of the hole. The bones are then pulled closer together and sutures tensioned via pulling on the loose suture ends 121 in the proximal direction allowing the individual performing the procedure to adjust the button-suture assembly 100 as necessary. Once the tensioning step is complete, the button-suture assembly 100 locks in place and holds the tension with preferably minimal relaxation or slip-back. The button-suture assembly 100 also allows for unlocking and loosening the assembly if re-tensioning or repositioning is desired by means of applying tension in the proximal direction to the locking pin 103 and causing it to translate proximally.

Figure 6:
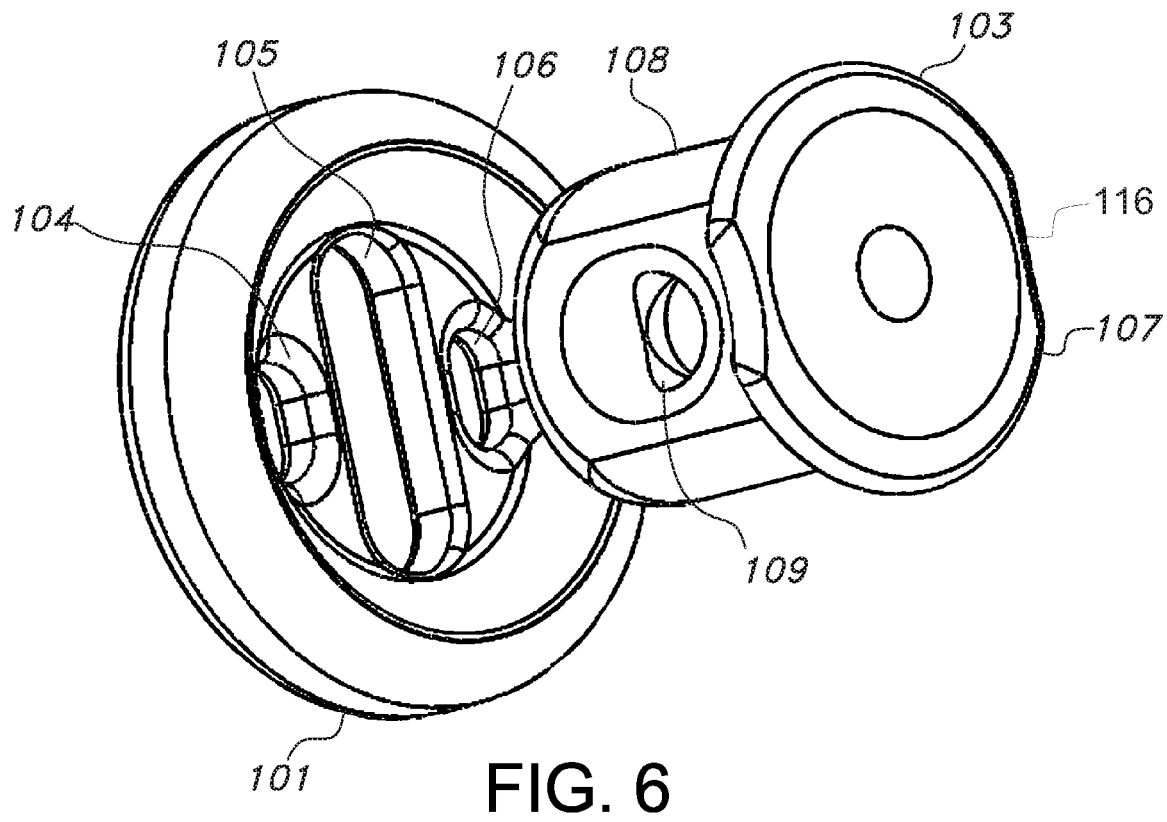
FIG. 6 depicts a perspective view of the button and locking pin of the button-suture assembly.

As will be appreciated by FIGS. 1-4, the preferred embodiment of the button-suture assembly 100 consists of a suspension device 115, a baseplate 110, and suture 102. The suspension device 115 is further comprised of a button 101 and a locking pin 103, as shown in FIG. 6. The button 101 is preferably round with three openings, the center opening 105 large enough to accept the distal member 108 of the locking pin 103, the first opening 104 configured to mate with the suture 102 and second opening 105 configured to mate with the suture 102 located on either side of the center opening 105 The locking pin 103 mates with the center opening 105 of the button 101 and includes a retaining mechanism configured to allow the sutures 102 to pass through the indented portions 116 of the locking pin 103 positioned against the interior surface 117 of the circumference of the button 101 when and preferably, only when tension is applied to the loose suture ends 121.

It should be understood that the indented portions 116 are optional and generally serve the purpose of compensating for the thickness of the suture 102 and allowing the locking pin 103 to sit closer to the button 101 thereby reducing the prominence of the suspension device 115 above the bone (can be seen in an embodiment in FIG. 7A). In an embodiment, the indented portions 116 may also serve the purpose constraining the side-to-side or rotational (excepting the twisting of the suture along its long axis) motion of the suture with the suspension device 115.

The distal member 108 of the locking pin 103 contains a transverse opening 109 through which the suture can pass. The indentations 116 of the locking pin 103 are located on opposite sides of the proximal end 107, which has a cross-sectional dimension greater than the opening of the button to prevent the locking pin from sliding out of the center button opening 105. Each indentation 116 creates a passage 118 for the sutures 102 between the locking pin 103 and button 101 creating pinch points 119. The indentations 116 have large surface area with rounded edges and flattened conical surfaces to preferably maximize the contact surface area between the suture 102 and the suspension device 115.

The pinch points 119 create locking (pinching) force to the tension stored in the suture loop 124, 125 and 126 of the assembly 100 as discussed above. Moreover, the indentations 116 of the locking pin 103 along with the individual openings 104 and 105 for each loose suture end 121 in this preferred embodiment help rotationally constrain the button-suture assembly 100 so that the sutures 102 do not twist (excepting the twisting of the suture along its long axis) while tensioning.

The baseplate 110 is preferably oblong in shape with at least two openings, but preferably four. In the preferred embodiment, the sutures loop three times through the two center openings 111 and 112 of the baseplate 110 forming the suture loops 124 and 125, two times through the transverse opening 109 of the locking pin 103 forming the suture loop 124, 125 and 126 and then through the two outer openings 104 and 106 of the button 101 and up through the pinch points 119 of the locking pin 103 as shown in FIG. 1. The two outer openings of the baseplate 113 and 114 can be used for additional and optional operations such as housing the "passing sutures" used to pull the baseplate 110 through the hole drilled in bone. Unlike the prior art, the pinch points 119 along with the individual openings 104 and 105 for each loose suture end 121 also allow for rotational control to prevent twisting (excepting the twisting of the suture 102 along its long axis) of the suture 102 during use.

Figure 2:
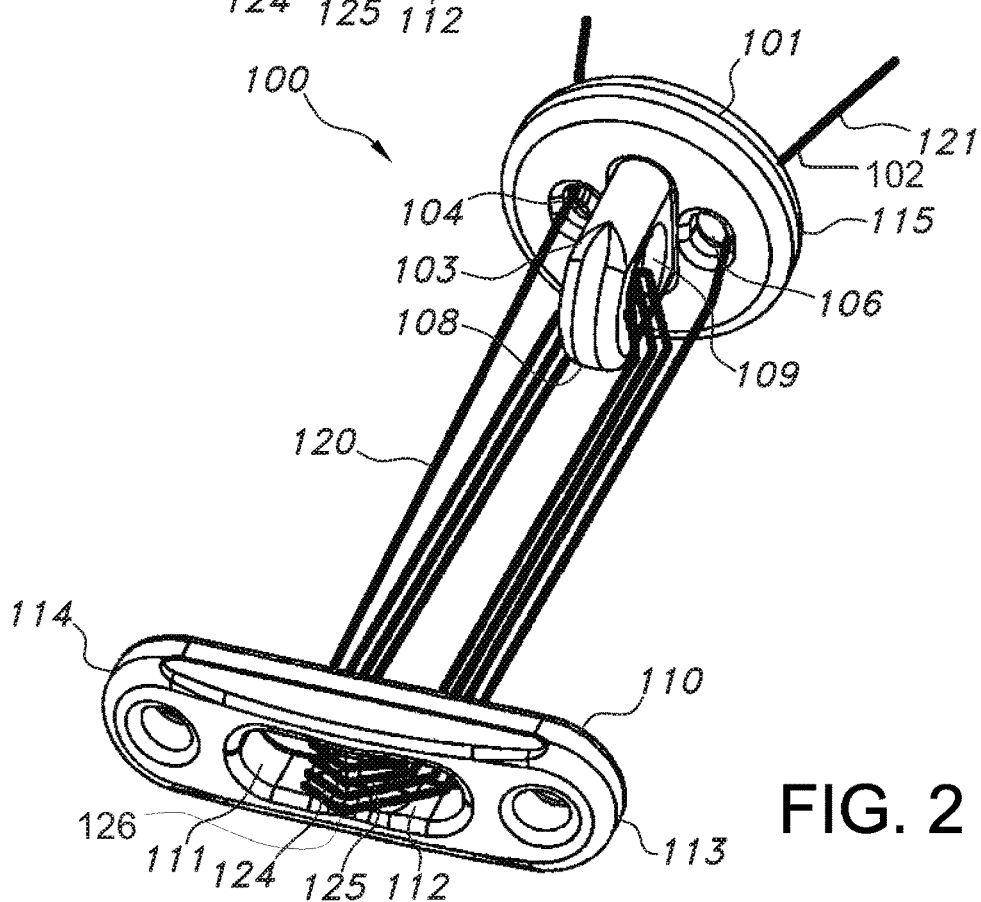
FIG. 2 depicts a perspective view of an embodiment of the button-suture assembly.
Figure 3:
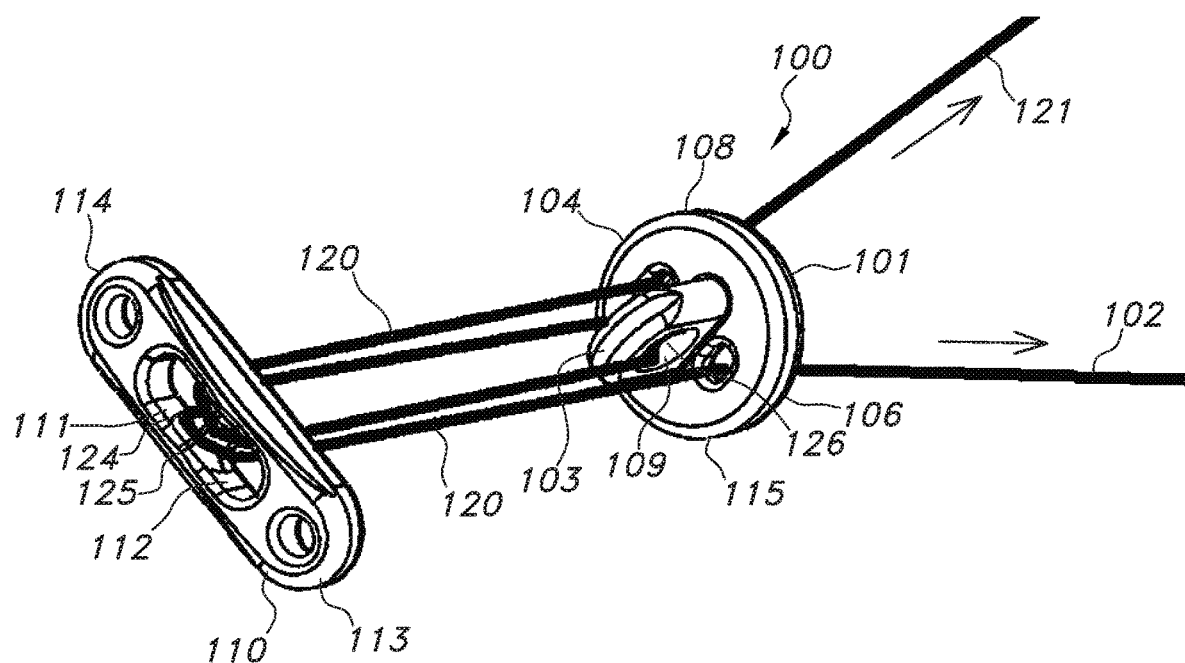
FIG. 3 depicts a perspective view of an embodiment of the button-suture assembly.

The button suture assembly 100 also contemplates the sutures 102 looping through the two center openings 111 and 112 of the baseplate 110 and transverse opening 109 of the locking pin 103 various numbers of time. For instance, as shown in FIG. 3, the sutures 102 may loop through the two center openings 111 and 112 of the baseplate 110 twice and through the transverse opening 109 of the locking pin 103 once to form the suture loops 124 and 125. Alternatively, the sutures may loop through the two center openings 111 and 112 of the baseplate 110 four times and through the transverse opening 109 of the locking pin 103 three times to form the suture loops 124 and 125, as depicted in FIG. 2. The increased number of suture loops (124 and 125) through the baseplate provides increased stability of the button suture assembly 100 and better procedure outcomes.

Figure 24:
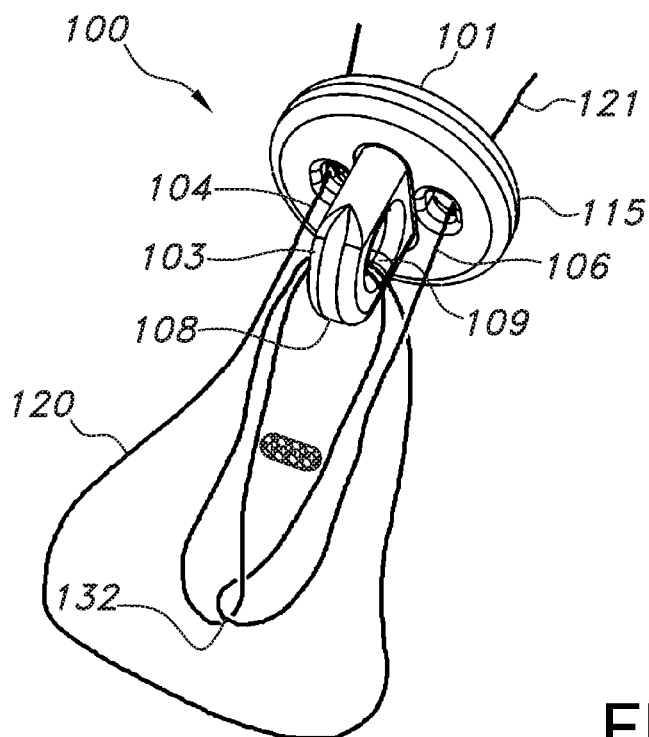
FIG. 24 depicts a perspective view of an embodiment of the button-suture assembly.
Figure 25:
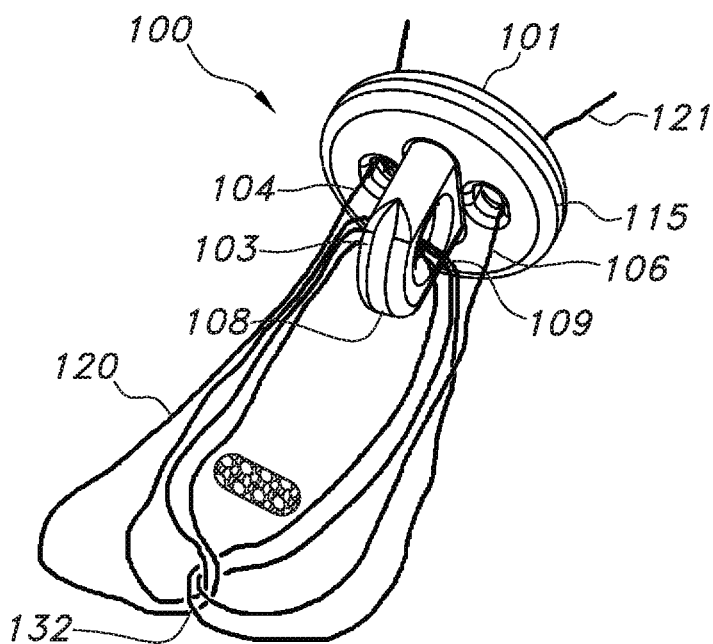
FIG. 25 depicts a perspective view of an embodiment of the button-suture assembly.

In an alternate embodiment, a baseplate is not used in the button-suture assembly 100. Instead, the sutures loop through each other and through the transverse opening 109 of the locking pin 103 two times to form the suture loops 132, as depicted in FIG. 24, to secure a graft or other members during a procedure. It is also contemplated that the sutures may loop through each other and through transverse opening 109 of the locking pin 103 three times to form the suture loops 132, as depicted in FIG. 25.

Figure 21:
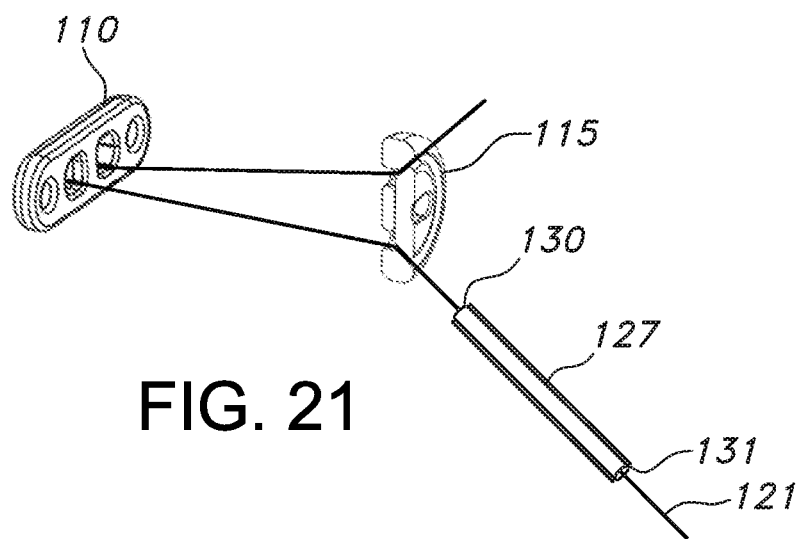
FIG. 21 depicts a perspective view of the sleeve member on the suture.
Figure 22:
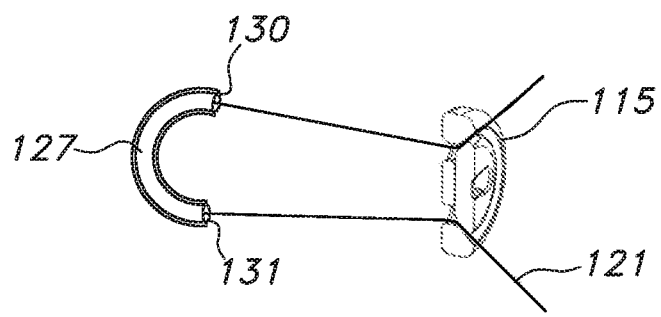
FIG. 22 depicts a perspective view of the sleeve member on the suture.
Figure 23:
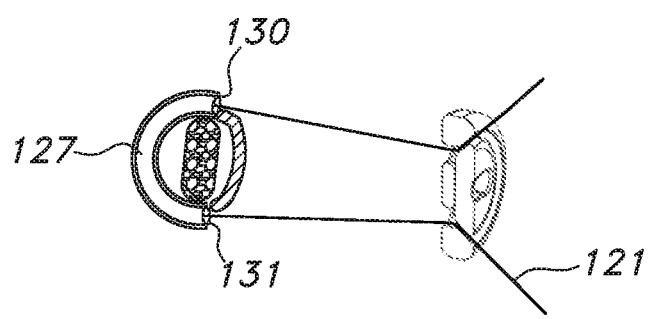
FIG. 23 depicts a perspective view of two sleeve members around a graft.

In another alternate embodiment, the baseplate 110 comprises a sleeve member 127 to tension the construct around the suture with an interior and an exterior surface along a length defined between a first end 130 and a second end 131, and at least two openings positioned along the length and extending from the interior and through the exterior surface, as shown in FIG. 22. Similar to the baseplate 110, the sleeve member 127 distributes the pressure evenly from the suture loops 124, 125 and 126 and helps reduce stress or damage to any structure that the sutures are looped around, including bone, tendons, tendon graft, other sutures or surgical tape. The sleeve member 127 should be smooth to prevent friction and sliding of the sutures 102 and can be woven to the suture 102 after assembly on both sides, as shown in FIG. 21. Also, as shown in FIG. 23, the sleeve member 127 can be used on both sides of a graft during graft procedures to prevent sliding of and damage to the graft.

Suture 102 is contemplated as being manufactured out of a variety of fibers or filaments including but not limited to polymer filaments (e.g. HMWPE, UHMWPE, PET, PTFE, PEEK, PEKK, PLA, PLLA, etc.), metallic filaments (e.g. Nitinol, Titanium, Titanium alloys, Tantalum, Stainless Steel, etc.) or organic filaments (e.g. Collagen, Silk, etc.) or other filaments such as carbon fiber or carbon nanotubes, etc. Suture 102 is further contemplated to comprise, but not limited to, a coreless suture, a suture with a jacket and a central core, a tape or any other tension member available or contemplated. The length of the suture 102 is contemplated as being between 150 mm and 1000 mm in length and more preferably between 300 mm and 1000 mm in length and most preferably between 250 mm and 750 mm in length. To prevent glove tears, surgeons can use hemostat forceps to roll the suture 102 during a procedure utilizing the button suture assembly 100.

Figure 8A:
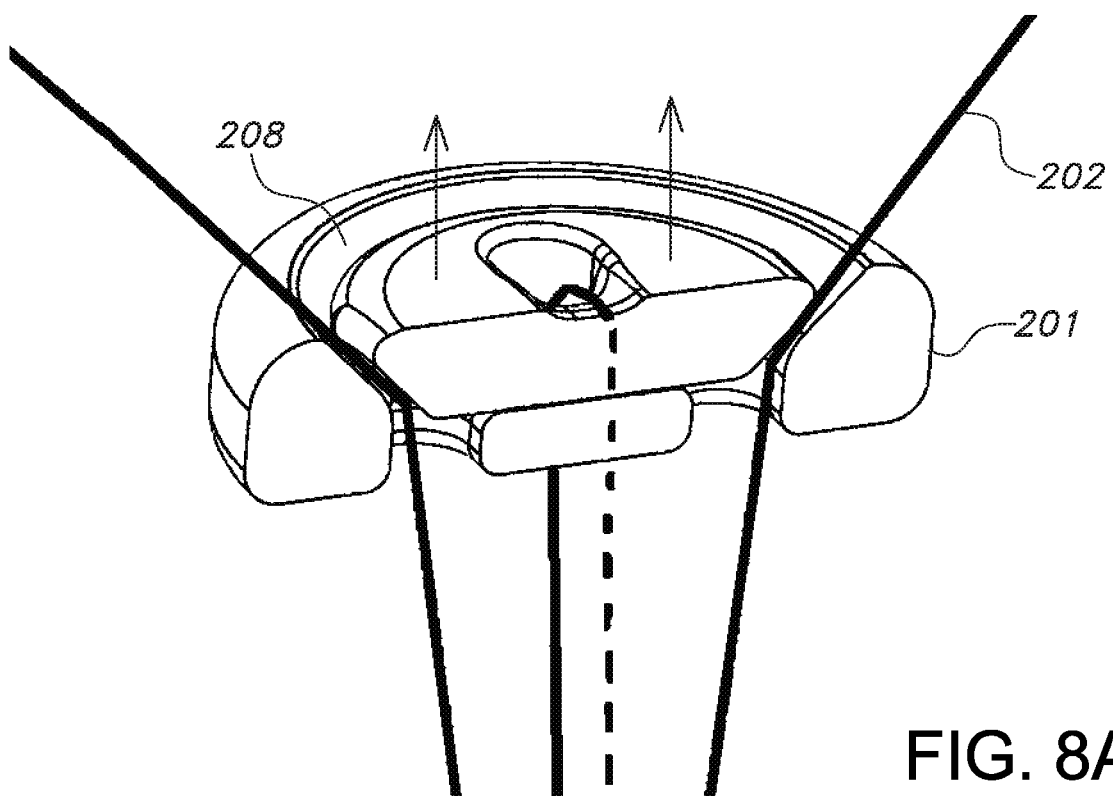
FIGS. 8A-8B depicts the unlocking mechanism of the suspension device. Individually.
Figure 8B:
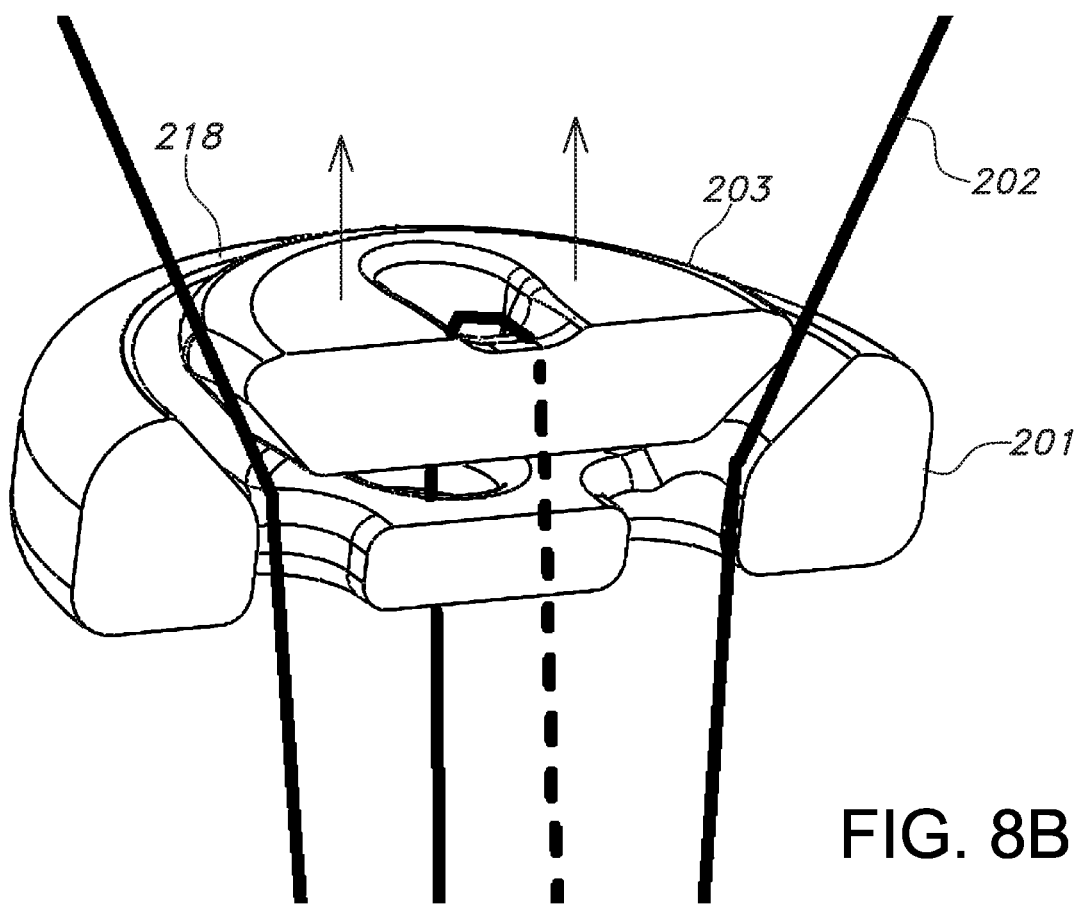

More specifically, after a hole is drilled through the surface of a bone or other member, the doubled-up suture 120 is passed through the indentions 116 of the suspension device 115 and tensioned by pulling on the ends 121 of the double suture 120 in the proximal direction, and locking the button-suture assembly 100 in place once the tensioning force is released as discussed above. As shown in FIG. 7B, when no pull is applied to the suture ends 121, the tension in the double loop 120 (or the suture loop 124, 125, 126) section prevents the loop from lengthening via sutures 102 being locked in the pinch points 119. Alternatively, pulling on the locking pin 103 unlocks the suspension device 115. In this state, the double suture loop 120 can be lengthened by pulling on the button 101, as shown in FIGS. 8A-8B.

Figure 14:
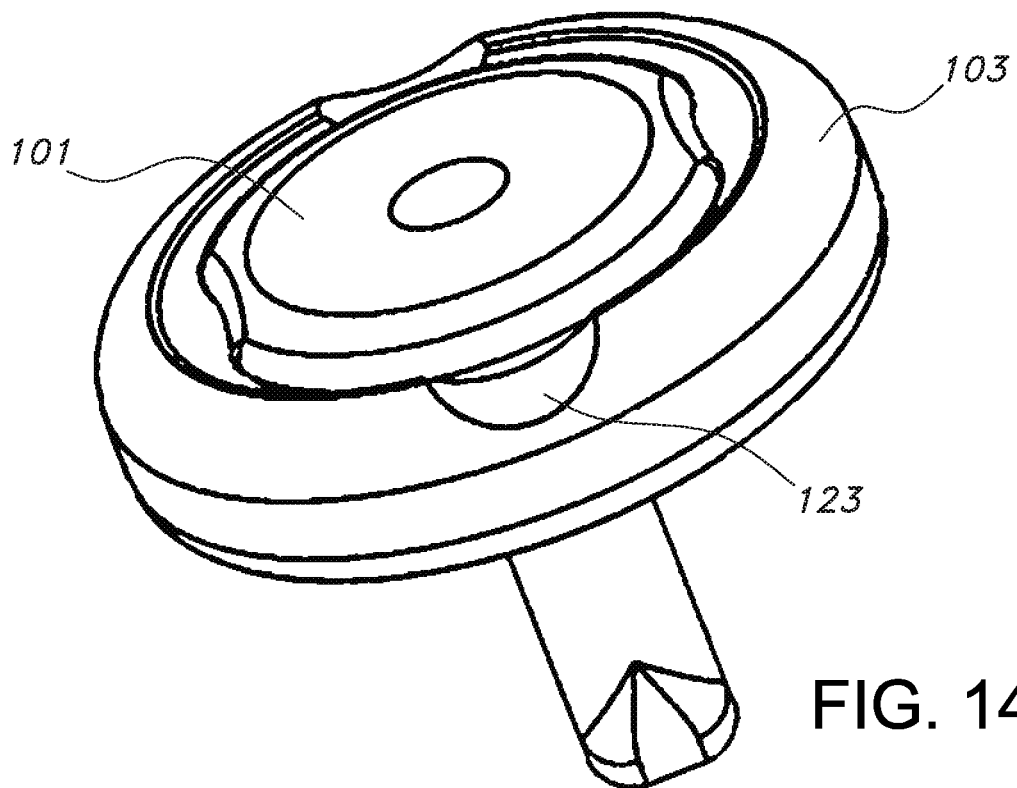
FIG. 14 depicts an embodiment of the locking pin with tool access cuts.
Figure 15:
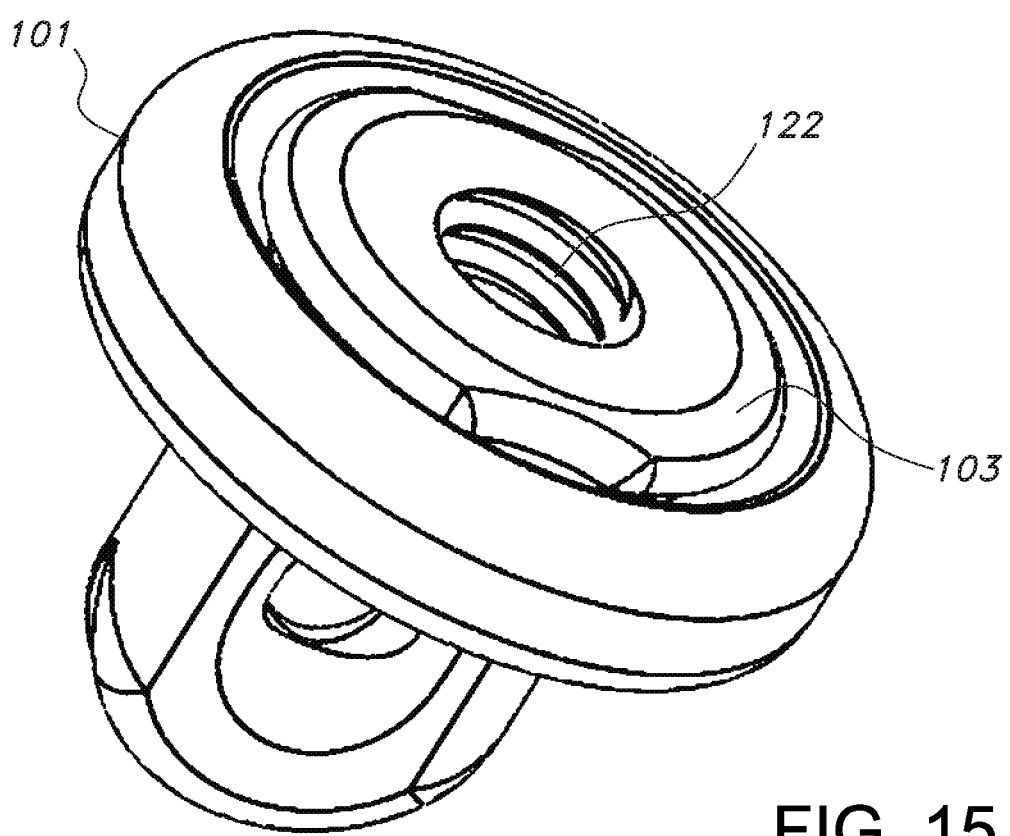
FIG. 15 depicts an embodiment of a threaded locking pin.
Figure 16:
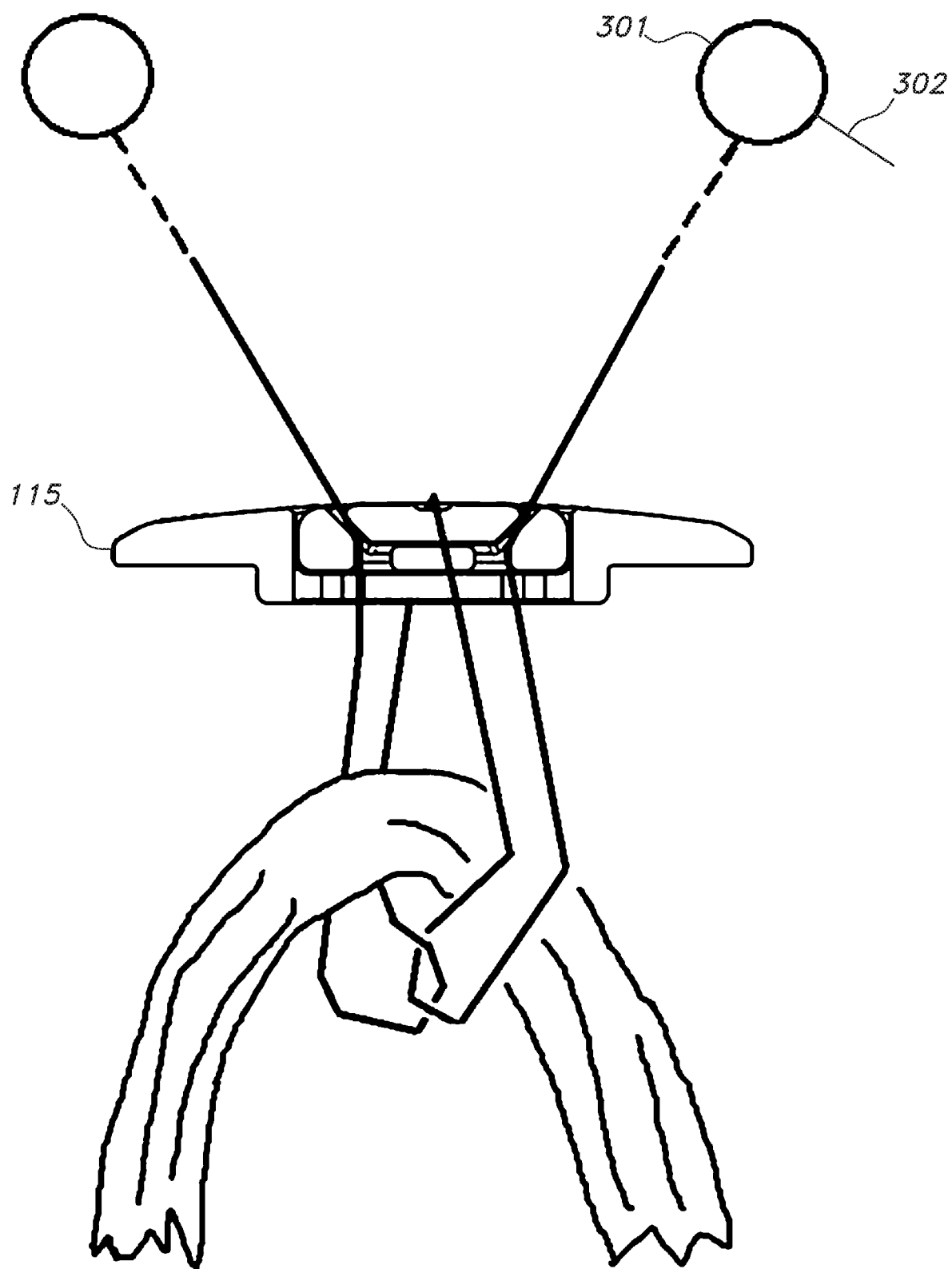
FIG. 16 depicts a top plan view of an embodiment of the button-suture assembly with pull rings.
Figure 17:
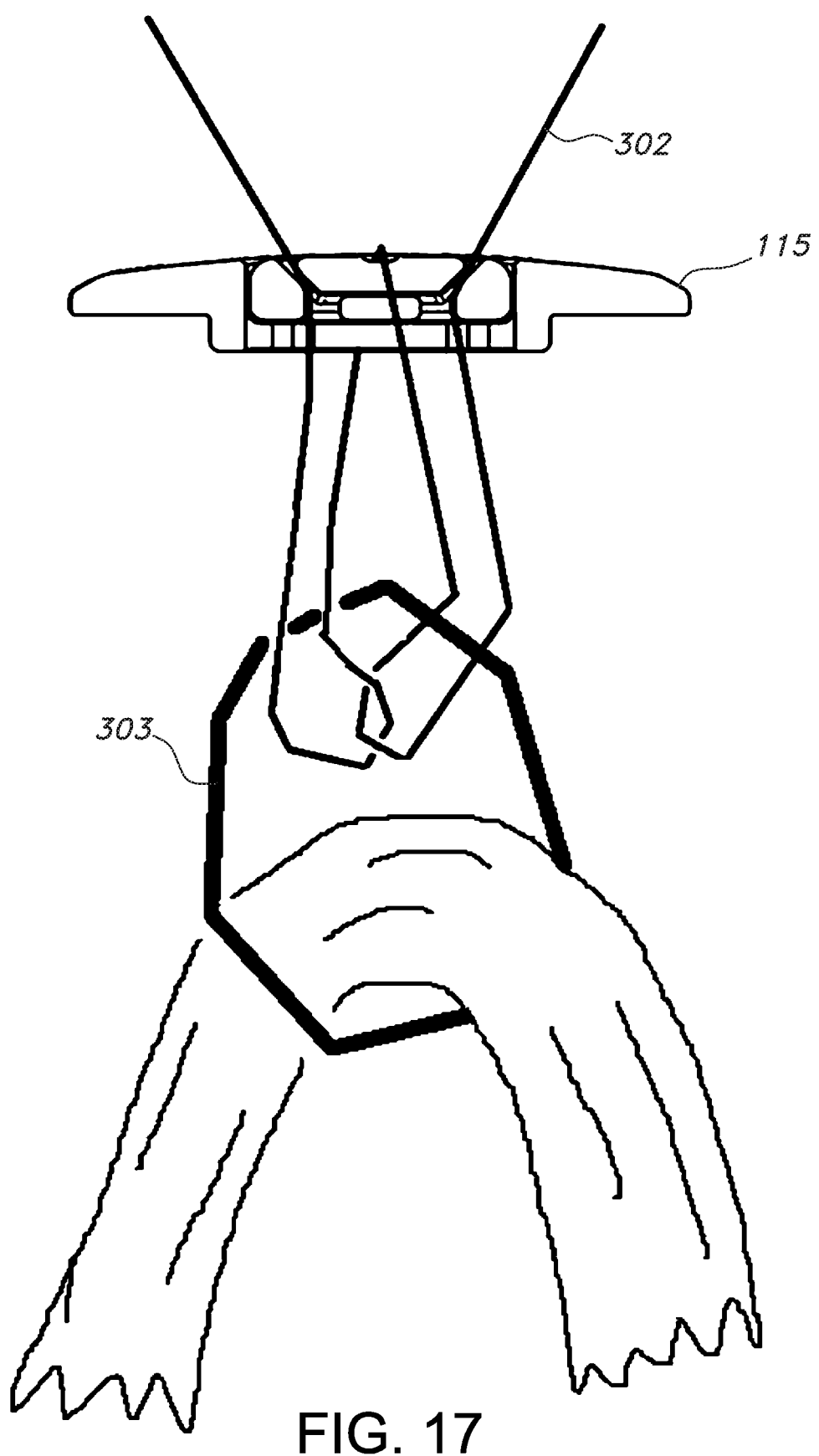
FIG. 17 depicts a top plan view of an embodiment of the button-suture assembly with a continuous loop.

The suspension device 115 can be unlocked in any way that separates the locking pin 103 from the button 101. These mechanisms include, but are not limited to, prying the locking pin 103 with a pick-like instrument, or the locking pin may 103 have specialized features for pulling it up with either general or specialized surgical instruments. In the preferred embodiment, the locking pin 103 is long enough that it can be pushed back through the suspension device from the distal side. The button-suture assembly 100 also contemplates various additional features to aid in the unlocking of the suspension device 115, such as a threaded locking pin 122 and tool access cuts 123 in the exterior of the button 101 as shown in FIGS. 14 and 16.

Figure 9:
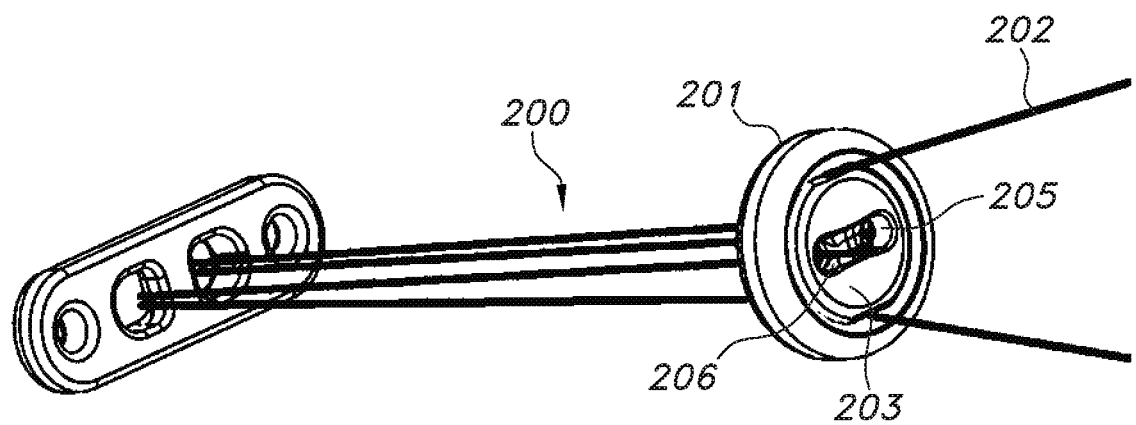
FIG. 9 depicts a perspective view of an embodiment of the button-suture assembly.
Figure 10:
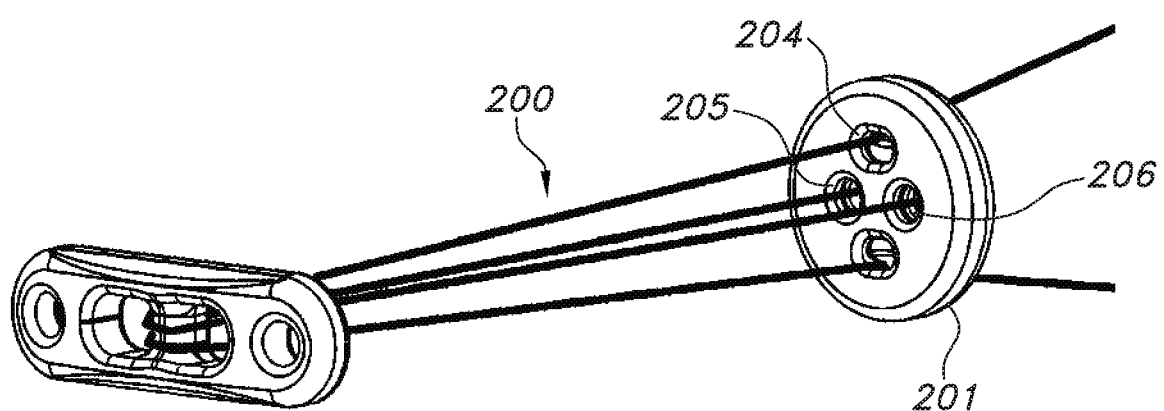
FIG. 10 depicts a perspective view of an embodiment of the button-suture assembly.

While the suspension device 115 described above is the preferred embodiment of the button-suture assembly 100, the tension can be maintained with the self-locking mechanism of the embodiment shown in FIG. 9. In this embodiment, the button 201 contains four openings in the interior surface which the flat locking pin 203 with two center holes 205 and 206 sits on top of, and the same baseplate 207 is used from the preferred embodiment. The sutures 202 pass through two of the button holes 205 and 206 in the same way they pass through the transverse opening 109 of the locking pin 103 forming the suture loop 204 equivalent in function to the suture loop 124, 125 and 126 of the embodiment of FIG. 1 for example, and up through indentations 208 on the sides of the modified locking pin 203. In this embodiment the locking mechanism does not control the rotation of the sutures while tensioning, primarily because the locking pin 203 is not translationally captured within the button 201 (i.e. can move indefinitely in the proximal dimension up to and including the point of disengaging from the suture 202).

Figure 13A:
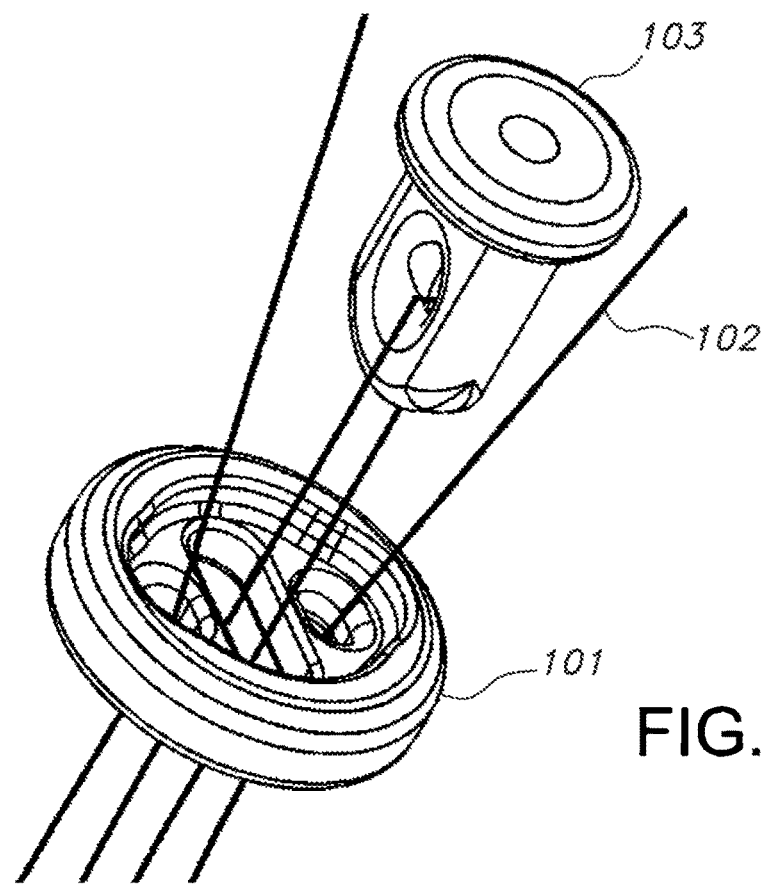
FIGS. 13A-13B depict an embodiment of the button with indentations. Individually.
Figure 13B:
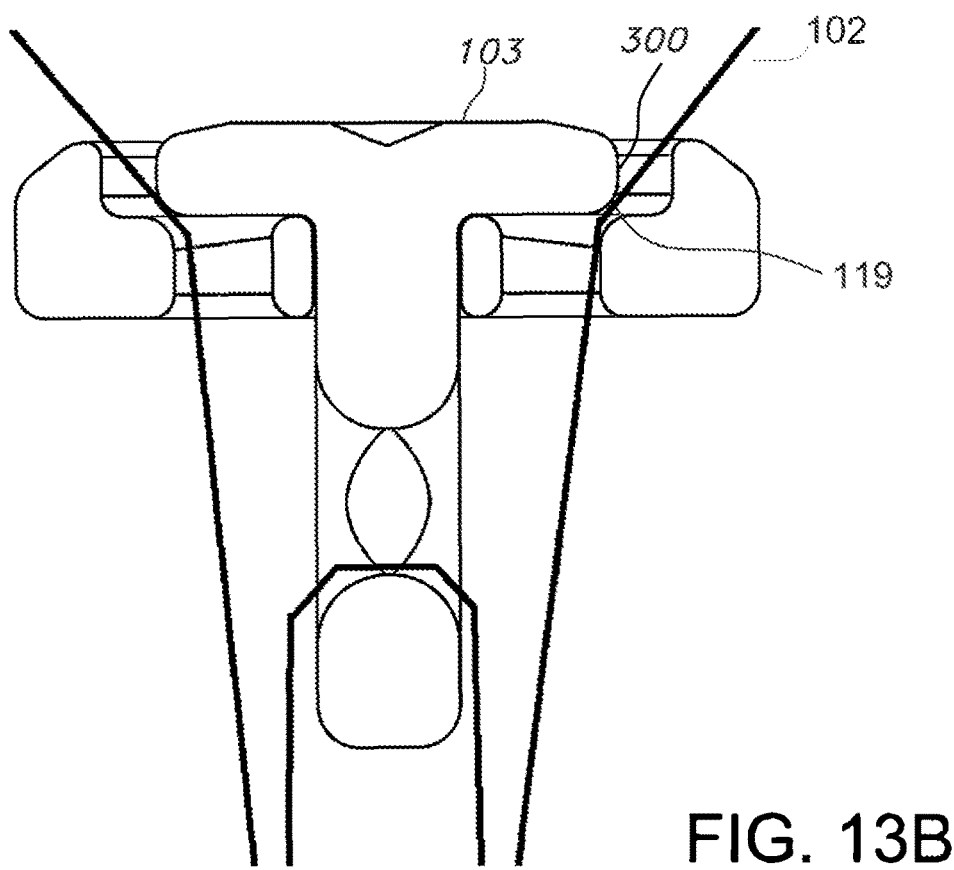

While the preferred embodiment of the invention contemplates tapered indentations 116 for the sutures to pass through with increased surface area, a generally rectilinear but rounded cross-section 300 of the proximal end of the locking pin 103 can also be used to form the pinch points 119, as shown in FIG. 13A-13B.

The button-suture assembly 100 can also utilize pull rings 301 for procedures such as tendon grafts. Pulling on suture-ends 121 to tension the button-suture assembly 100 could be uncomfortable to a user, so the pull-rings 301 are contemplated to improve the ergonomics of this step. In this embodiment, the pull rings 301 are located at the suture ends 302 to reduce loop length. The pull rings 301 can be made out of woven, braided or embroidered fiber or comprise solid metal or polymer components. Also, a thicker continuous loop 303 is utilized rather than the doubled suture suspension loop 120 of the preferred embodiment. The increased surface area of the continuous loop 303 is intended to prevent the "sawing" effect on the tendon graft by better distributing the stresses.

Figure 11A:
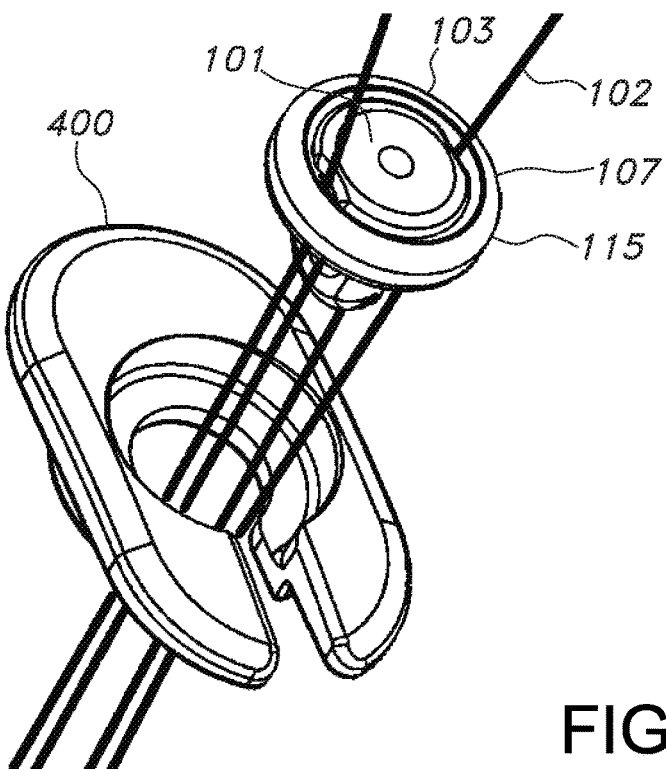
FIGS. 11A-11B depict a perspective view of an embodiment of the button-suture assembly and footprint extender. Individually.
Figure 11B:
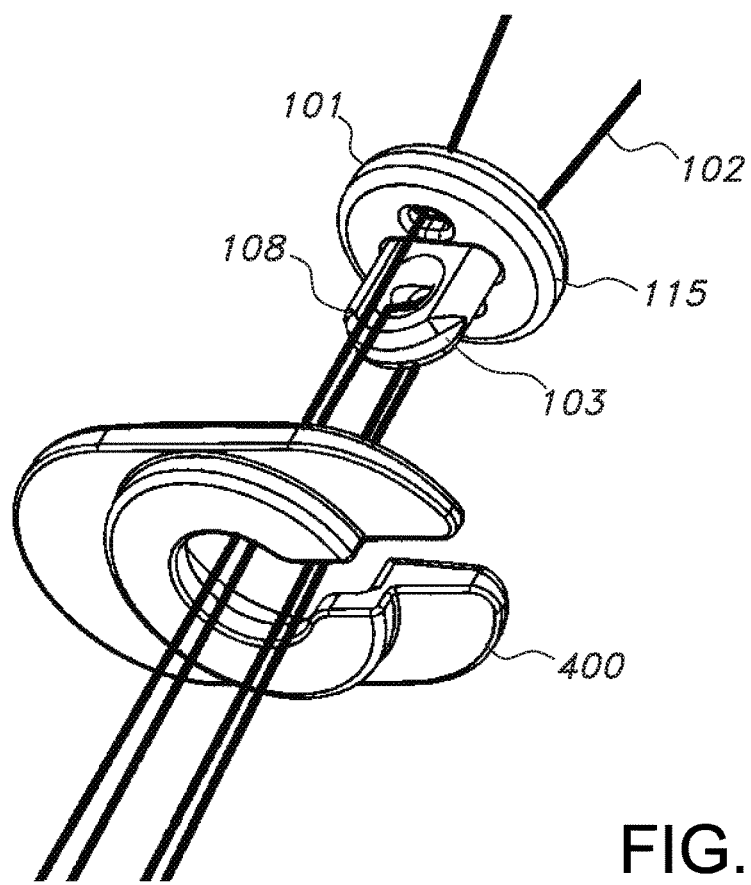

The button-suture assembly 100 is generally compatible with drilled bone holes of generally smaller diameter than largest dimension of the button 101. However, a footprint extender 400 can be added to the suspension device 115 in any embodiment to accommodate bone or other holes of diameters larger than the largest dimension of the button 101. In the preferred embodiment, the footprint extender 400 contains an opening 401 on one side allowing the footprint extender 400 to slide around and envelop the suspension device 115, as can be appreciated in FIG. 11A. As shown in FIG. 11B, the interior of the footprint extender 402 is hollow allowing the sutures from the suspension device 115 to pass to and from the baseplate 110 without obstruction.

Figure 12A:
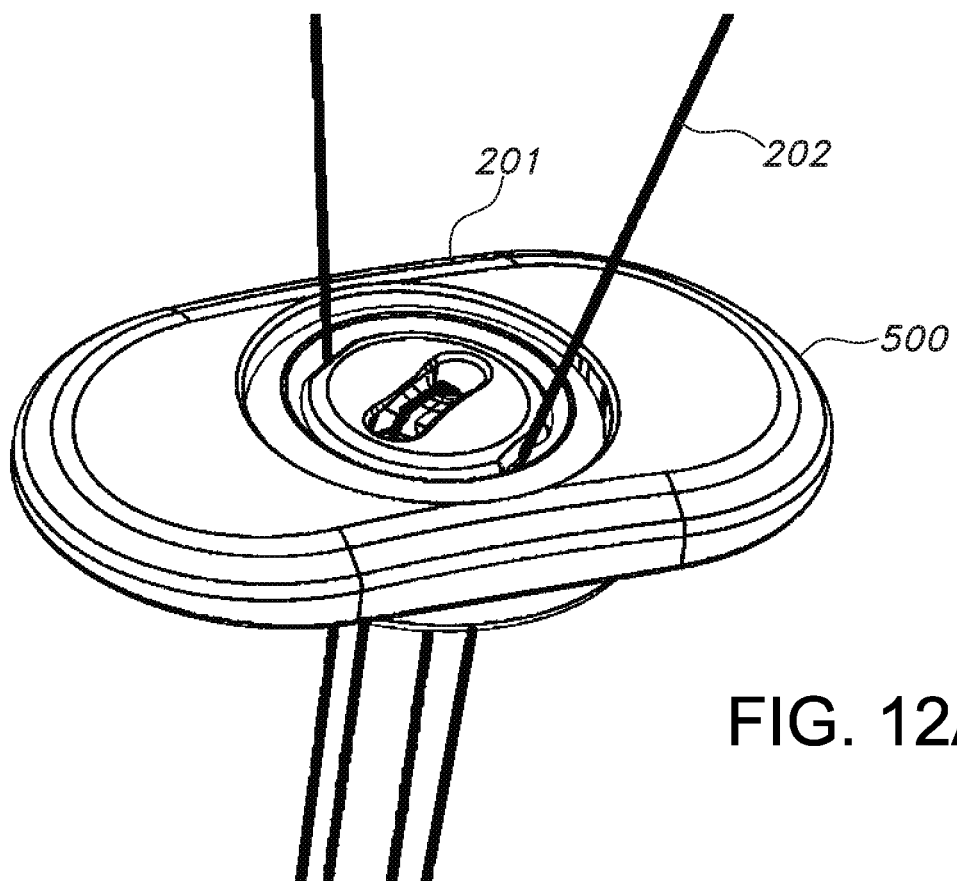
FIGS. 12A-12D depict an embodiment of the button-suture assembly with footprint extender. Individually.
Figure 12B:
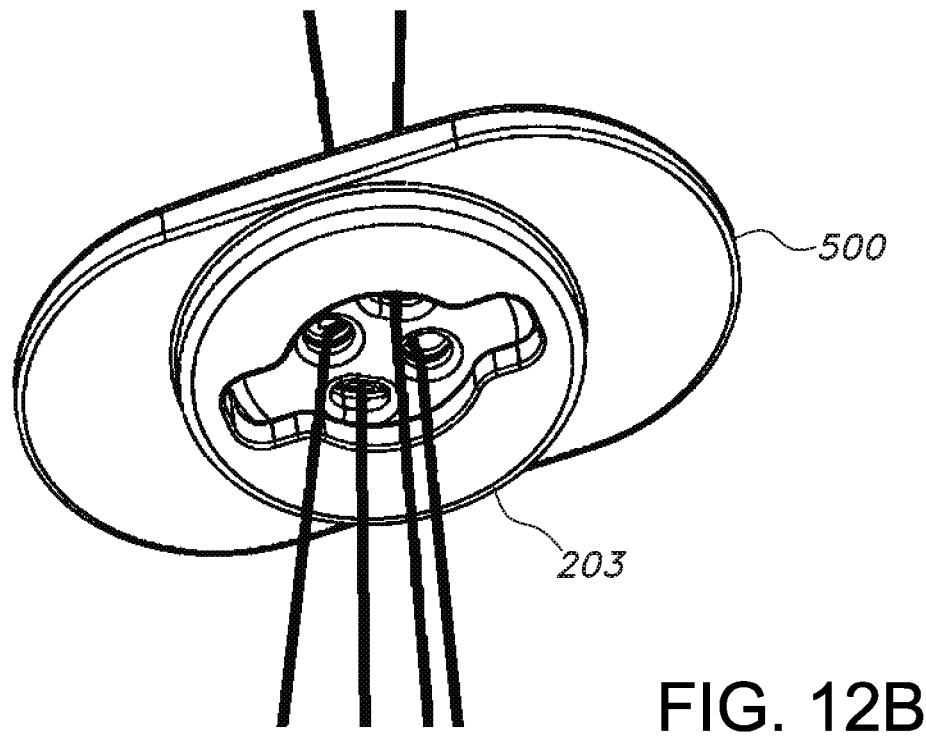
Figure 12C:
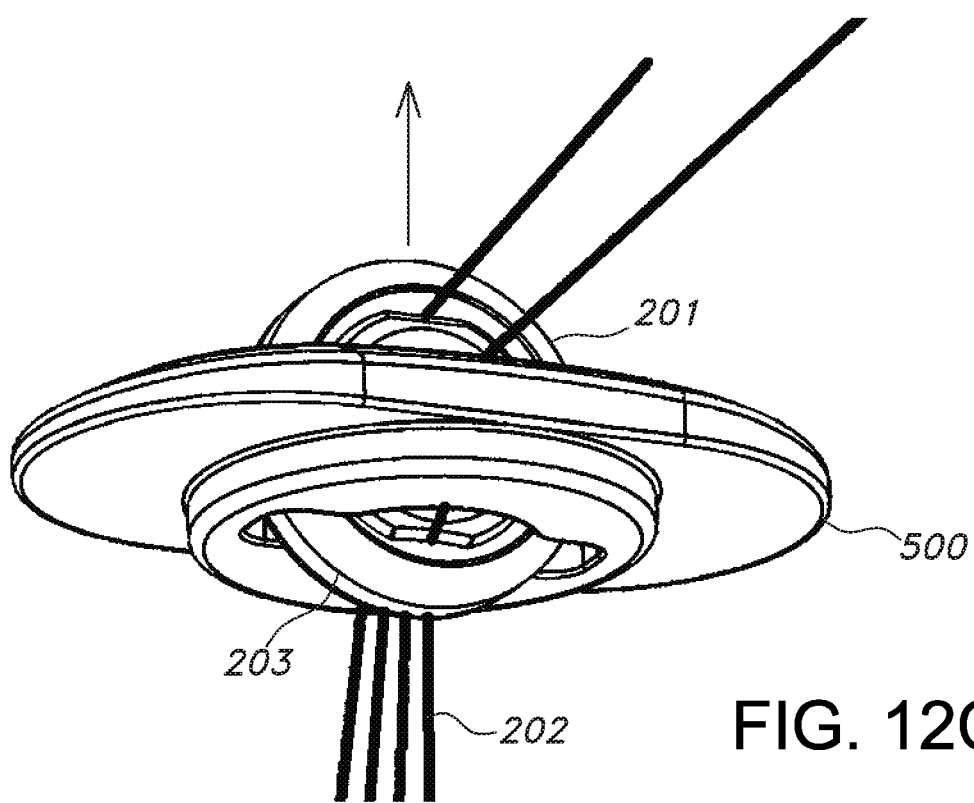
Figure 12D:
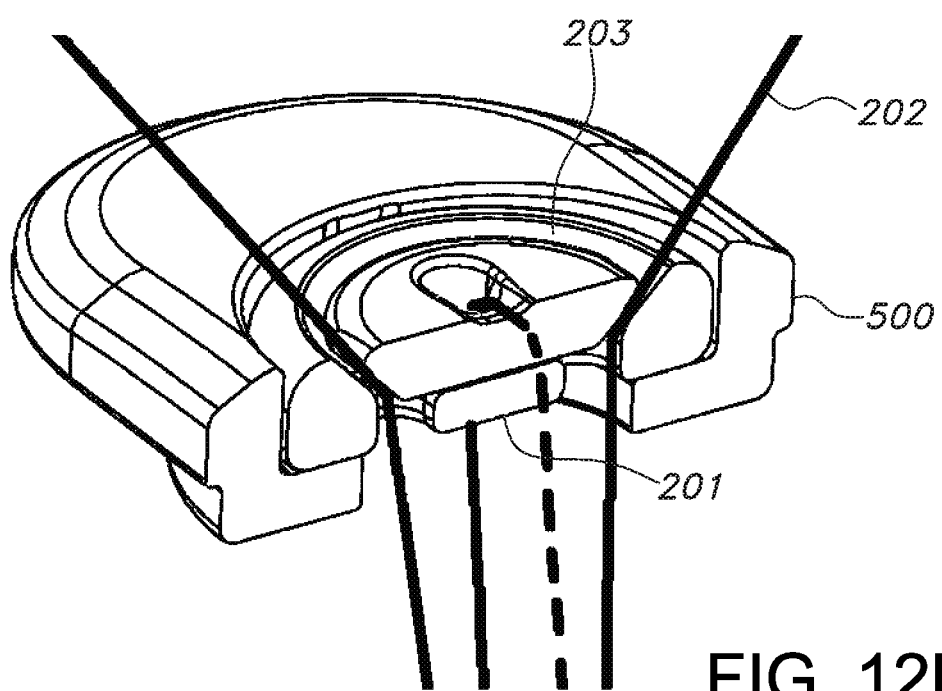

In the second embodiment, the footprint extender 500 mirrors the exterior shape of the suspension device in a larger scale and envelops the suspension device allowing the sutures 202 to again pass through without obstruction, as shown in FIG. 12B. As shown in FIGS. 12C and 12D, the suspension device 217 can be pulled through and snapped into the footprint extender 500.

Figure 18A:
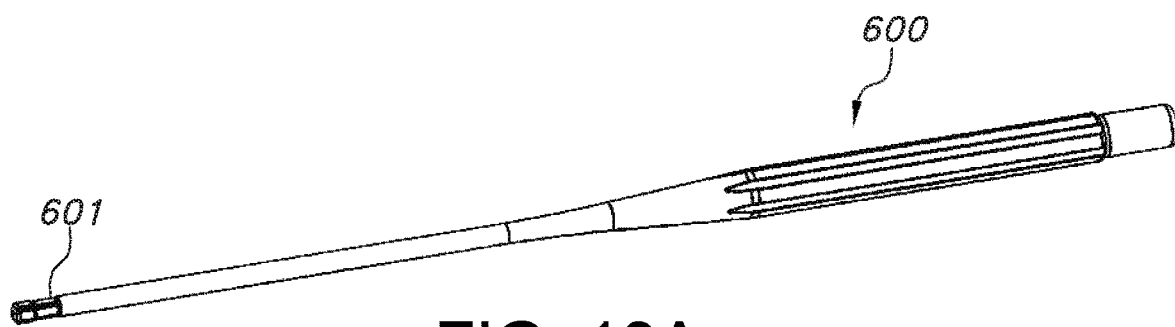
FIGS. 18A-18C depicts an expandable sounder instrument. Individually.
Figure 18B:
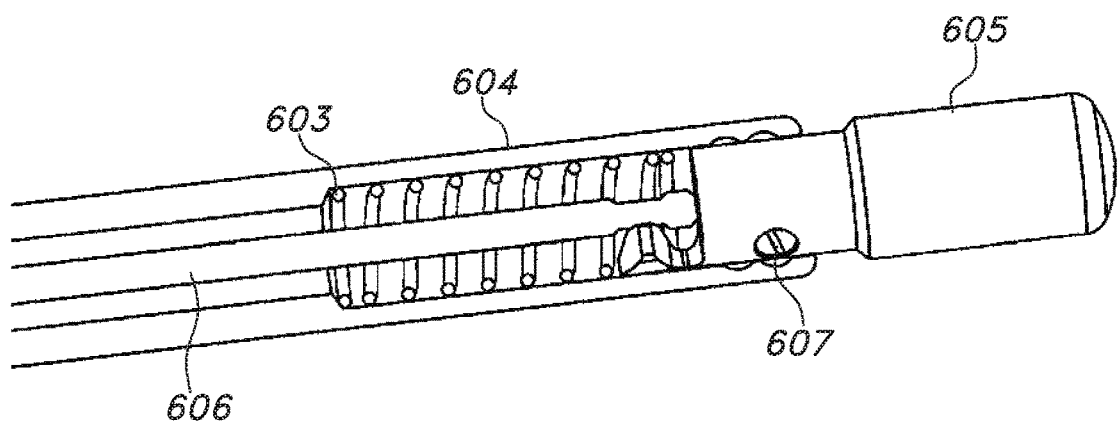
Figure 18C:
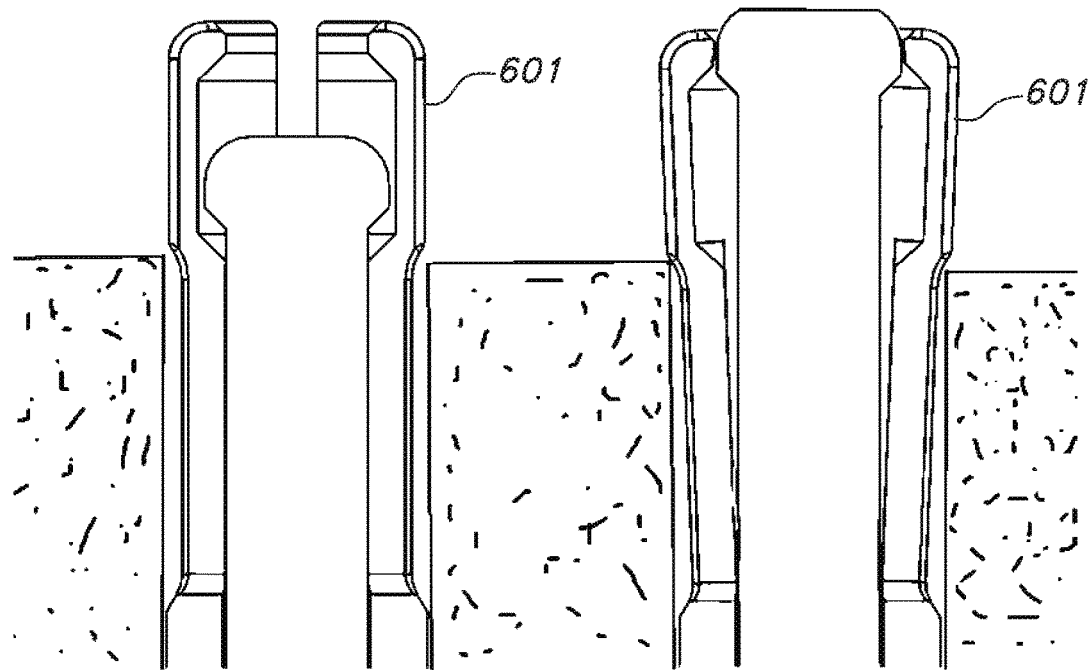

Surgical procedures which would use the button-suture assembly 100 may benefit from the aid of an expandable sounder instrument 600 as shown in FIG. 18A. The expandable sounder instrument 600 is comprised of a tip 601, inner shaft 606, compression spring 603, sounder body 604, spring plunger 607, and push button 605, and is used to assess whether a drilled hole breaks through the distal cortex of bone. If the sounder tip 601 is located past the distal cortex, then pressing the push button 605 and expanding the tip 601 will result in the user not being able to pull the sounder instrument 601 out of the hole because the tip 601 is larger than the hole diameter when expanded. Specifically, when the push button 605 of the sounder instrument 600 is pressed engaging the compressing spring 603, the diameter of the tip 601 of the instrument is expanded and unable to exit the hole in the bone, as shown in FIG. 18C.

Figure 19A:
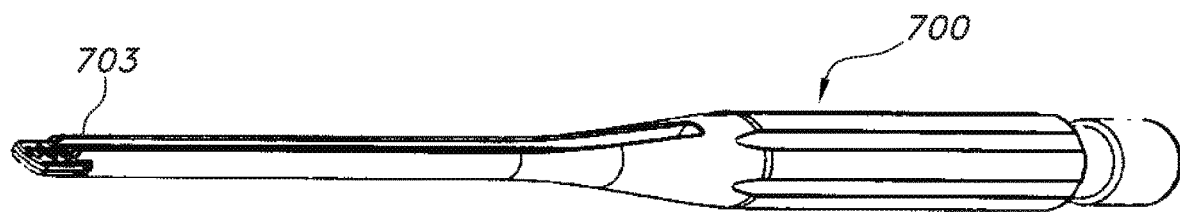
FIGS. 19A-19E depict a button inserter/flipper. Individually.
Figure 19B:
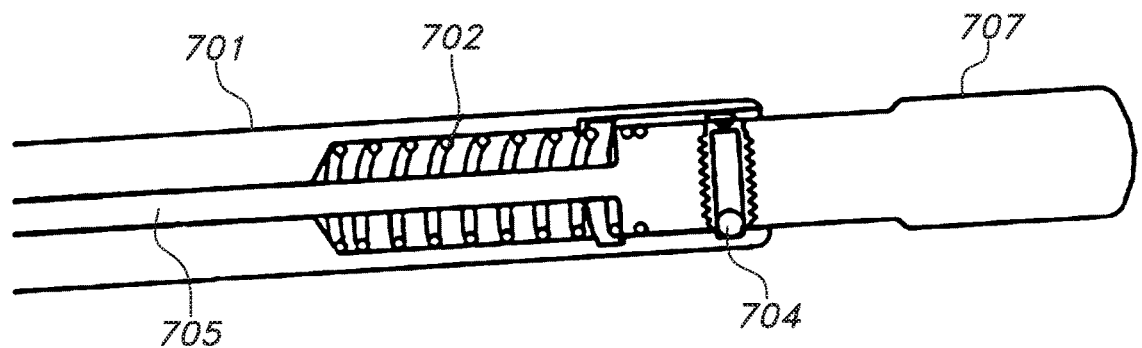
Figure 19C:
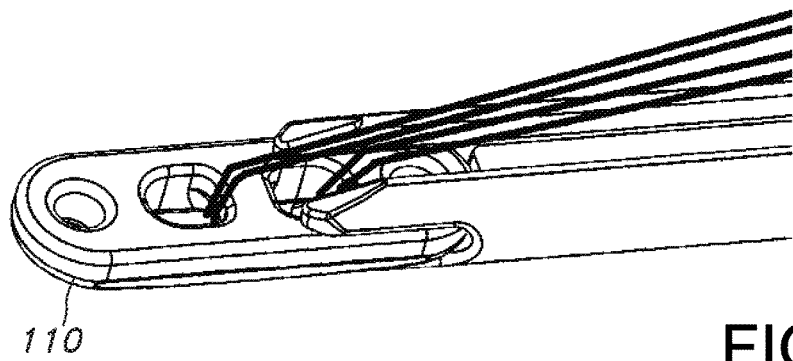
Figure 19D:
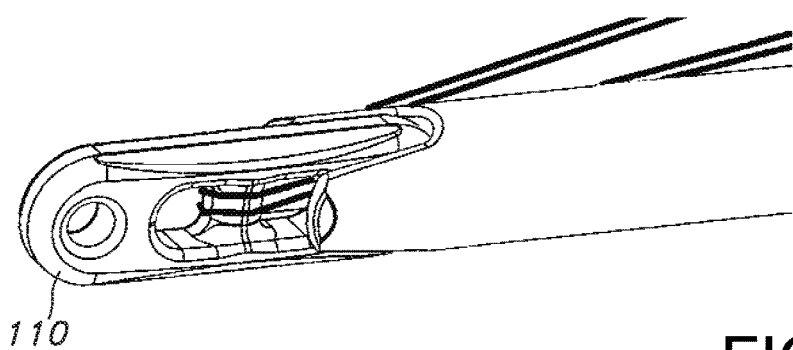
Figure 19E:
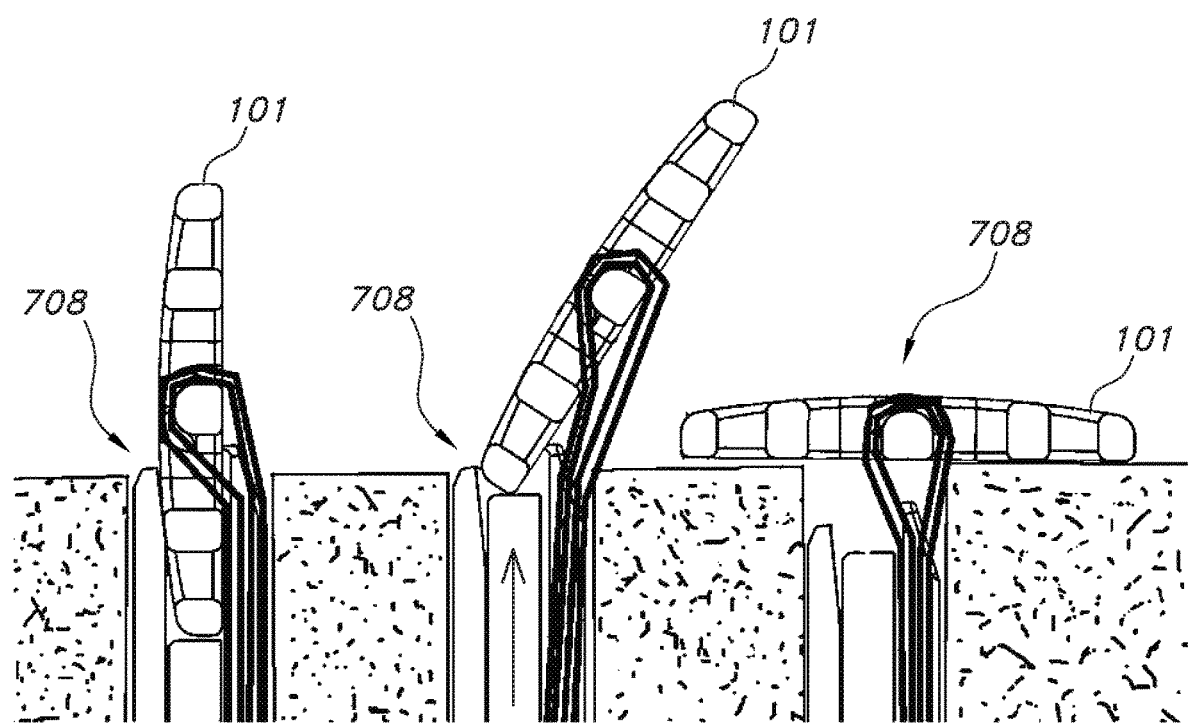

Also, a button inserter/flipper 700 can be used in surgical procedures in which the button-suture assembly 100 is employed. The button inserter/flipper 700 depicted in FIGS. 19A-19B is comprised of a main body 701, compression spring 702, tip 703 push button 707, spring plunger 704, and inner shaft/flipper 705. The button/inserter flipper 700 inserts the button-suture assembly 100 through a bone bore and flips it behind the distal cortex in a forward motion. The button suture assembly 100 is loaded into the tip 703 of the instrument and existing sutures 102 are passed along the lengthwise groove and lightly tensioned to facilitate passing through the hole 708. The button inserter/flipper 700 is then inserted into the drilled hole 708. When the button 101 is past the distal cortex, it is flipped by simultaneously applying tension on the sutures 102 and pushing the proximal push button 707 fully as shown in FIG. 19E. The button 101 may provide tactile feedback when fully pressed by means of spring plunger 704. While button/inserter flippers 700 known in the art flip the button in a retrograde motion, the tension is actually maintained in the button-suture assembly 100 and allows for forward actuation of the button 101. The button inserter/flipper 700 is then withdrawn from the hole 708, leaving a flipped button 101 on the distal bone surface.

Figure 20:
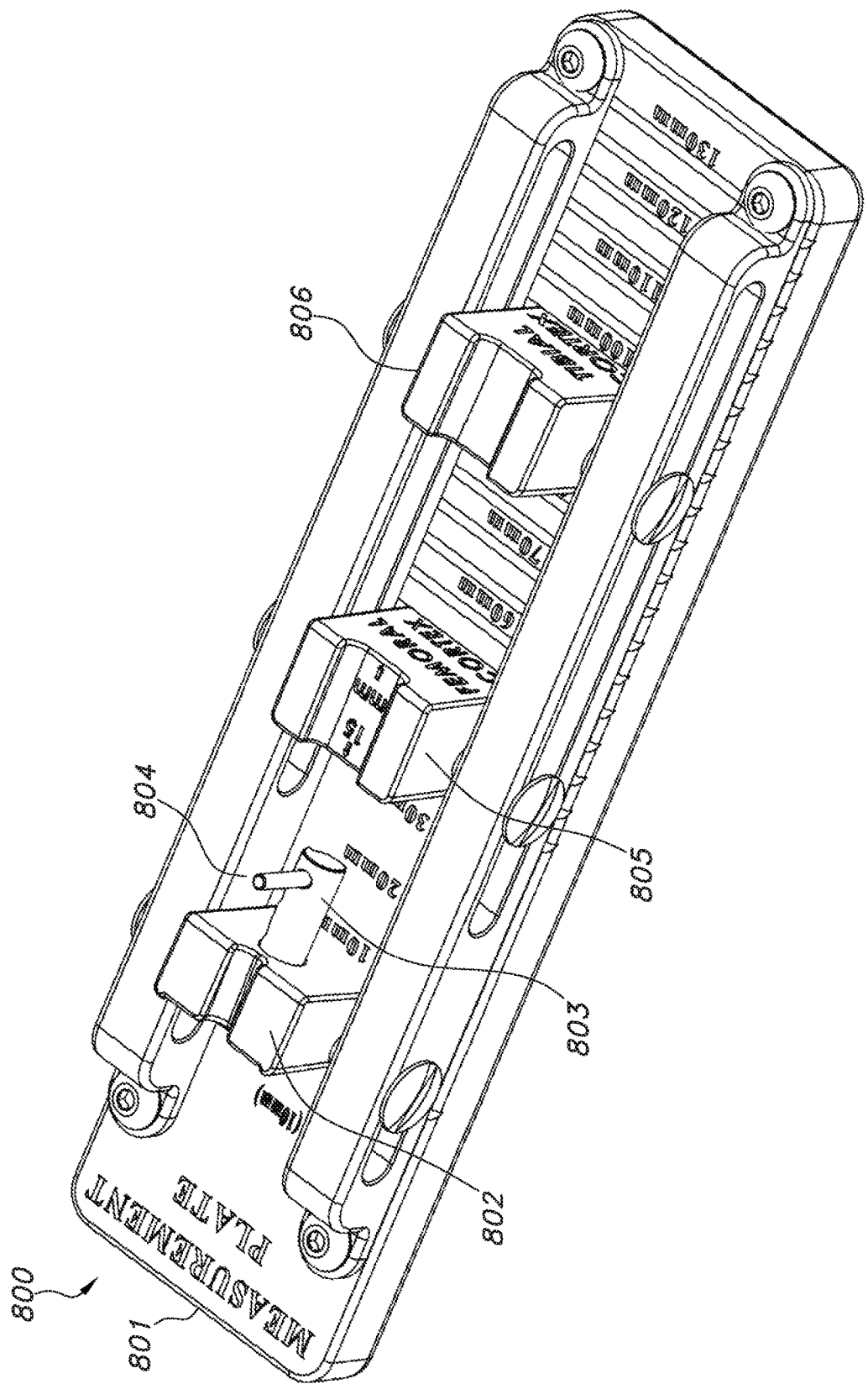
FIG. 20 depicts a perspective view of a measurement plate.

Finally, a measurement plate 800 as shown in FIG. 20 is an auxiliary tool for implantation of the button-suture assembly 100. The measurement plate 800 comprising a measurement base 801, a primary reference member 802, a secondary reference member 803, an engagement feature 804, a tertiary reference member 805, and a terminal reference member 806.

The measurement base 801 provides a means to measure the length of a surgical corridor and distances in-between; for example, the canal for anterior cruciate ligament (ACL) repair. Length measurements are marked about the measurement plate's 800 primary axis. The primary reference member 802 can be positioned to indicate a primary frame of reference. In this example, it would indicate a starting measurement point at the distal femoral cortex in an ACL repair.

The secondary reference member 803 is adjustable in position about the axis of the primary reference member 802. The adjustable position of the secondary reference member 803 could indicate a second measurement; in this example, it would indicate the length of a loop attached to a button as used in ACL repair. The secondary reference member 803 can have an engagement feature 804 which could serve the purpose of attaching an item to aid in or simulate the procedure. In this case, it could be used to hold one end of a surgical graft used in ACL repair. Holding the graft would allow for a simulated view of how the graft is positioned and/or measured relative to the femur and tibia. The T, adjustable in position about the primary axis of the measurement base 801, can be positioned to indicate a secondary measurement or location. In this example, the tertiary reference member 805 can be positioned to indicate the proximal femoral cortex in ACL repair. The distance between the primary reference member 802 and the tertiary reference member 805 would equal the total length of the femoral bone tunnel.

The terminal reference member 806, adjustable in position about the primary axis of the measurement base 801, can be positioned to indicate a third measurement or location. In this example, the terminal reference member 806 can be positioned to indicate the proximal tibial cortex in ACL repair. The distance between the primary reference member 802 and the terminal reference member 806 would be the overall length as measured from the distal cortex of the femur to the proximal cortex of the tibia.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation. Additionally, it should be understood that the various embodiments of the suspension device described herein contain optional features that can be individually or together applied to any other embodiment shown or contemplated here to be mixed and matched with the features of that device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

What is claimed is:

1. An orthopedic stabilization device comprising:
a button having a plurality of openings;
a locking pin configured to mate with the button through a center opening in the button, the locking pin having a proximal end, a distal end, and a threaded aperture formed in the proximal end; and
a tensioning member having two tensioning member ends passing through a first opening and a second opening in the button and disposed outwardly towards a proximal direction of the button, wherein the tensioning member forms one or more tensioning member loops by at least passing through a transverse opening in a distal member of the locking pin.

2. The orthopedic stabilization device as claimed in claim 1, wherein the locking pin further comprises two indentations located on the proximal end of the locking pin disposed along the first opening and the second opening respectively to create two corresponding passages between the locking pin and an interior surface of the circumference of the button for the tensioning member to pass through.

3. The orthopedic stabilization device as claimed in claim 2, wherein the passages allow a proximal movement of tensioning member when a pulling force is applied to the tensioning member ends towards the proximal direction.

4. The orthopedic stabilization device as claimed in claim 3, wherein the passages prevent a distal movement of tensioning member when the pulling force ceases to exist subsequent to the applying of the pulling force to the tensioning member ends.

5. The orthopedic stabilization device as claimed in claim 1, wherein the tensioning member corresponds to one of: a coreless suture, a suture with a jacket and a central core, and a tape.

6. The orthopedic stabilization device as claimed in claim 1, wherein the threaded aperture is configured to engage an instrument.

7. The orthopedic stabilization device as claimed in claim 6, wherein the instrument is an unlocking tool.

8. A knotless button-suture assembly for orthopedic stabilization, the button-suture assembly comprising:
a button having a first opening, a second opening and a center opening;
a tensioning member having two tensioning member ends exiting from the first opening and the second opening of the button and disposed in the proximal direction; and
a locking pin mated with the button through the center opening of the button in such a manner that:
allows a proximal movement of the tensioning member when a pulling force is applied to the two tensioning member ends towards a proximal direction; and
prevents a distal movement of the tensioning member when the pulling force applied to the two tensioning member ends ceases to exist;
wherein the locking pin has a proximal end, a distal end, and a threaded opening formed in the proximal end and configured to threadedly engage an instrument.

9. The knotless button-suture assembly as claimed in claim 8, wherein the locking pin comprises a proximal member and a distal member and wherein the distal member has a transverse opening.

10. The knotless button-suture assembly as claimed in claim 8, wherein the locking pin has two indentations located on the proximal member of the locking pin disposed along the first opening and the second opening respectively to create two corresponding passages between the locking pin and an interior surface of the circumference of the button for the tensioning member to pass through.

11. The knotless button-suture assembly as claimed in claim 10, wherein the locking pin mated with the button creates one or more pinch points in the two passages when the pulling force ceases to exist after the applying of the pulling force to the two tensioning member ends.

12. The knotless button-suture assembly as claimed in claim 8, wherein the instrument comprises an unlocking tool.

* * * * *